(12) United States Patent
Fallin et al.

(10) Patent No.: US 8,192,465 B2
(45) Date of Patent: Jun. 5, 2012

(54) INTERSPINOUS PROCESS SPACERS

(75) Inventors: Thomas Wade Fallin, Hyde Park, UT (US); Joshua A. Butters, Chandler, AZ (US); Greta Jo Hays, Logan, UT (US)

(73) Assignee: MedicineLodge. Inc., Logan, UT (US)

( * ) Notice: Subject to any disclaimer, the term of this patent is extended or adjusted under 35 U.S.C. 154(b) by 874 days.

(21) Appl. No.: 12/100,482

(22) Filed: Apr. 10, 2008

(65) Prior Publication Data

US 2008/0255668 A1   Oct. 16, 2008

Related U.S. Application Data

(60) Provisional application No. 60/910,834, filed on Apr. 10, 2007.

(51) Int. Cl.
*A61B 17/70* (2006.01)
(52) U.S. Cl. ........................................ 606/249
(58) Field of Classification Search .......... 606/246–249, 606/250; 623/17.11, 17.16
See application file for complete search history.

(56) References Cited

U.S. PATENT DOCUMENTS

| | | | |
|---|---|---|---|
| 6,068,630 A | 5/2000 | Zucherman et al. | |
| 6,074,390 A | 6/2000 | Zucherman et al. | |
| 6,149,652 A | 11/2000 | Zucherman et al. | |
| 6,152,926 A | 11/2000 | Zucherman et al. | |
| 6,238,397 B1 | 5/2001 | Zucherman et al. | |
| 6,280,444 B1 | 8/2001 | Zucherman et al. | |
| 6,375,682 B1 | 4/2002 | Fleischmann | |
| 6,379,355 B1 | 4/2002 | Zucherman et al. | |
| 6,419,676 B1 | 7/2002 | Zucherman et al. | |
| 6,440,169 B1 | 8/2002 | Elberg et al. | |
| 6,478,796 B2 | 11/2002 | Zucherman et al. | |
| 6,500,178 B2 | 12/2002 | Zucherman et al. | |
| 6,626,944 B1 * | 9/2003 | Taylor | 623/17.16 |
| 6,733,534 B2 | 5/2004 | Sherman | |
| 6,796,983 B1 | 9/2004 | Zucherman et al. | |
| 6,893,464 B2 | 5/2005 | Kiester | |
| 7,163,558 B2 | 1/2007 | Senegas et al. | |
| 2004/0181282 A1 | 9/2004 | Zucherman et al. | |
| 2004/0199255 A1 | 10/2004 | Mathieu et al. | |
| 2004/0220568 A1 | 11/2004 | Zucherman et al. | |
| 2005/0010293 A1 | 1/2005 | Zucherman et al. | |
| 2005/0143738 A1 | 6/2005 | Zucherman et al. | |
| 2005/0228383 A1 | 10/2005 | Zucherman et al. | |
| 2005/0245937 A1 | 11/2005 | Wislow | |
| 2005/0261768 A1 | 11/2005 | Trieu | |
| 2006/0084983 A1 | 4/2006 | Kim | |
| 2006/0084985 A1 | 4/2006 | Kim | |
| 2006/0084988 A1 | 4/2006 | Kim | |

(Continued)

*Primary Examiner* — Eduardo C Robert
*Assistant Examiner* — Summer Kostelnik
(74) *Attorney, Agent, or Firm* — Peter K. Johnson; James Larson; G. Jo Hays

(57) ABSTRACT

Interspinous implants including a spacer configured to fit between first and second adjacent spinous processes of a human spine, to maintain a minimum separation between the spinous processes. An implant also includes a fixation portion coupled to the spacer, in which the fixation portion engages at least one spinous process to hold the spacer in a stable position relative to the spinous process. An implant may be monolithic, non-fillable, and may be inserted between the spinous process from a lateral approach. The fixation portion may be configured as a bracket which can substantially encircle the spinous process, or as flanges which engage lateral sides of the spinous process(es). The spacer may be resilient, and may be expandable along the anterior/posterior direction between the spinous processes. An implant may provide resilient resistance during extension, and/or a uniform extension stop between the spinous processes.

31 Claims, 27 Drawing Sheets

U.S. PATENT DOCUMENTS

| | | |
|---|---|---|
| 2006/0085069 A1 | 4/2006 | Kim |
| 2006/0085070 A1 | 4/2006 | Kim |
| 2006/0089654 A1 | 4/2006 | Lins et al. |
| 2006/0184247 A1 | 8/2006 | Edidin et al. |
| 2007/0032790 A1 | 2/2007 | Aschmann et al. |
| 2007/0161992 A1* | 7/2007 | Kwak et al. ................. 606/61 |

* cited by examiner

INTERSPINOUS PROCESS SPACERS

CROSS-REFERENCE TO RELATED APPLICATIONS

This application claims the benefit of the following, which are incorporated herein by reference:

pending U.S. Provisional Patent Application No. 60/910,834, filed Apr. 10, 2007, and is entitled INTERSPINOUS PROCESS SPACER FOR UNILATERAL INSERTION; and pending U.S. Provisional Patent Application No. 60/916,098, filed May 4, 2007, and is entitled INTERSPINOUS PROCESS SPACER WITH AT LEAST TWO FLANGES AND ONE TETHER.

BACKGROUND OF THE INVENTION

The invention relates to interspinous devices which may be used to separate the vertebrae in order to relieve pain and/or other symptoms caused by a collapse of the normal intervertebral spacing. The present invention generally describes an interspinous process spacer which may be placed between two adjacent spinous processes to provide a minimum separation between the two spinous processes.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention relates to orthopedic devices and related implantation instruments and methods. Although the examples provided herein relate to an interspinous spacer, the systems and methods described herein may be readily adapted for a wide variety of implants and procedures. Accordingly, the scope of the present invention is not intended to be limited by the examples discussed herein, but only by the appended claims.

Figure 1:
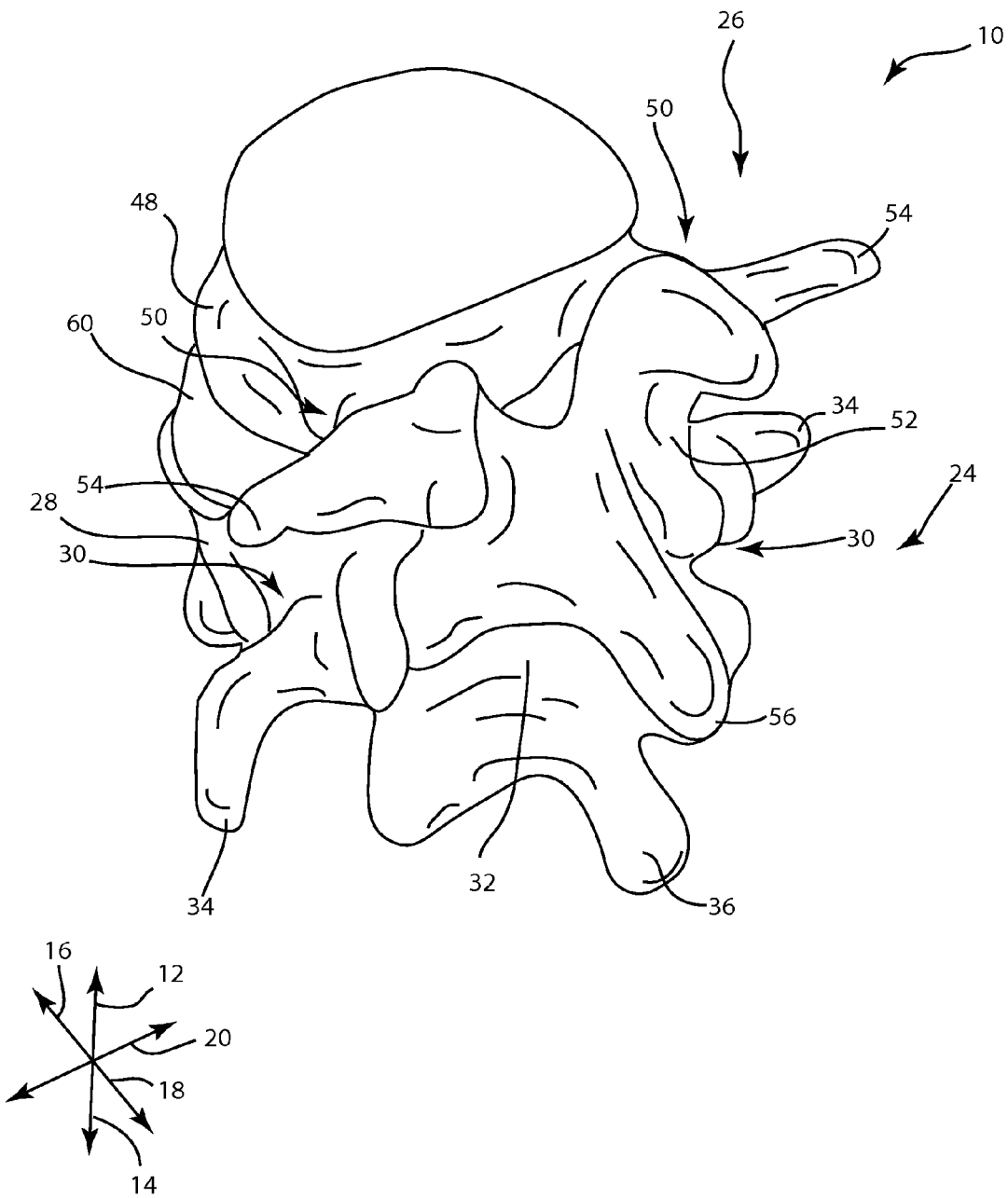
FIG. 1 is a perspective view of a portion of a spine.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral"

refers to a position or orientation relatively further from the sagittal plane. In this application, "superior" refers to a position or orientation in the cephalad direction 12, and "inferior" refers to a position or orientation in the caudal direction 14.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54, each of which extends from the corresponding pedicle 50 generally along the medial/lateral axis 20, and a spinous process 56 that extends from the lamina 52 along the posterior direction 18. The vertebrae 24, 26 are separated from each other by an intervertebral disc 60.

Figure 2:
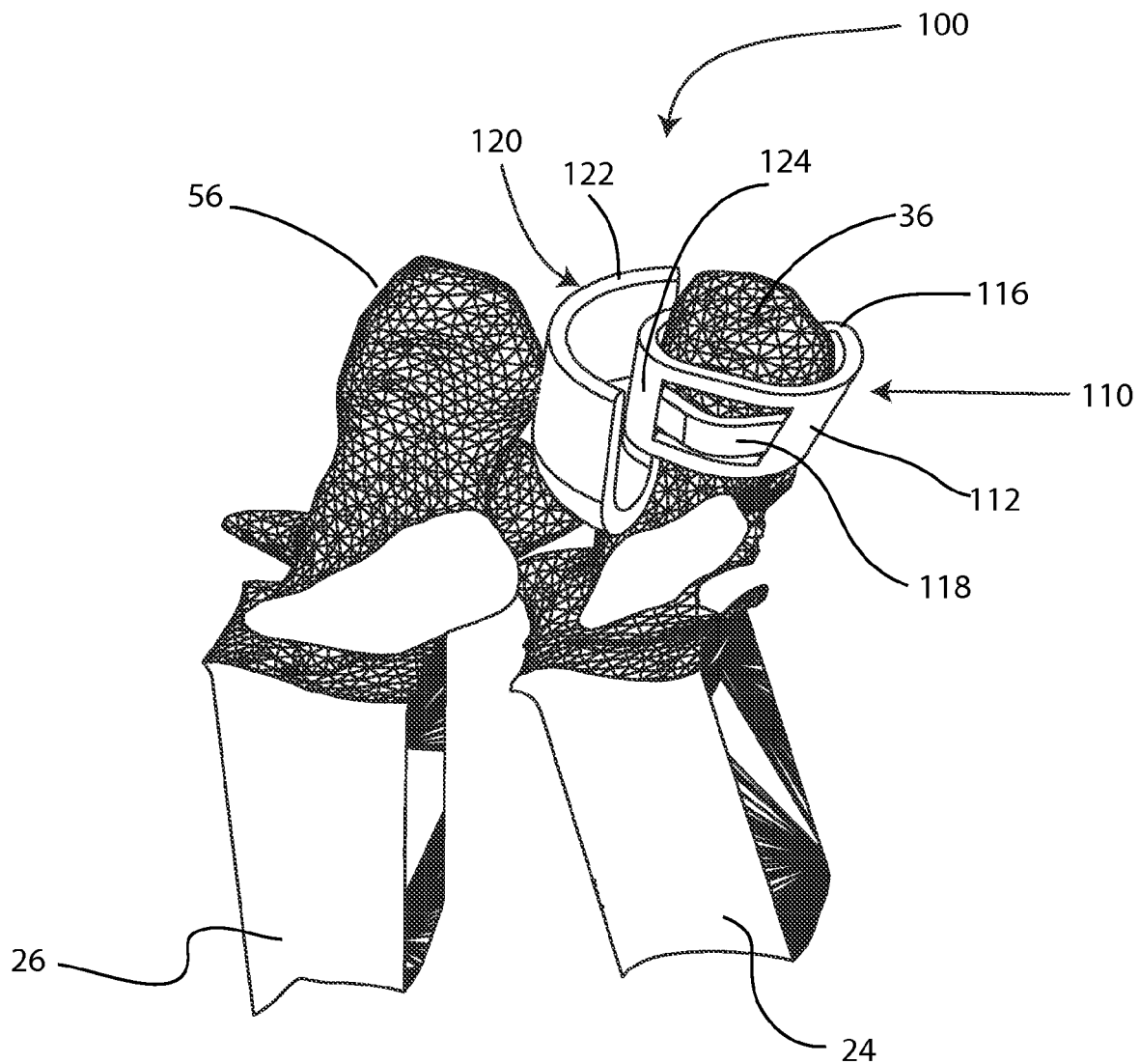
FIG. 2 is a lateral perspective view of an interspinous spacer implant implanted between two vertebrae in a portion of a spine.

Referring to FIG. 2, a perspective view illustrates one embodiment of an implant 100, which may be termed an interspinous spacer, implanted between two adjacent vertebrae 24, 26. Implant 100 comprises a fixation portion which is a bracket 110, joined to a spacer 120. The bracket 110 may comprise a collar 112 which is shaped to substantially encircle and grip the spinous process 36. The collar has a first end 114 (shown in FIG. 3A) and a second end 116, and rims may be formed at the opposing ends of the collar 112 to assist the collar in securely gripping the spinous process.

Figure 3A:
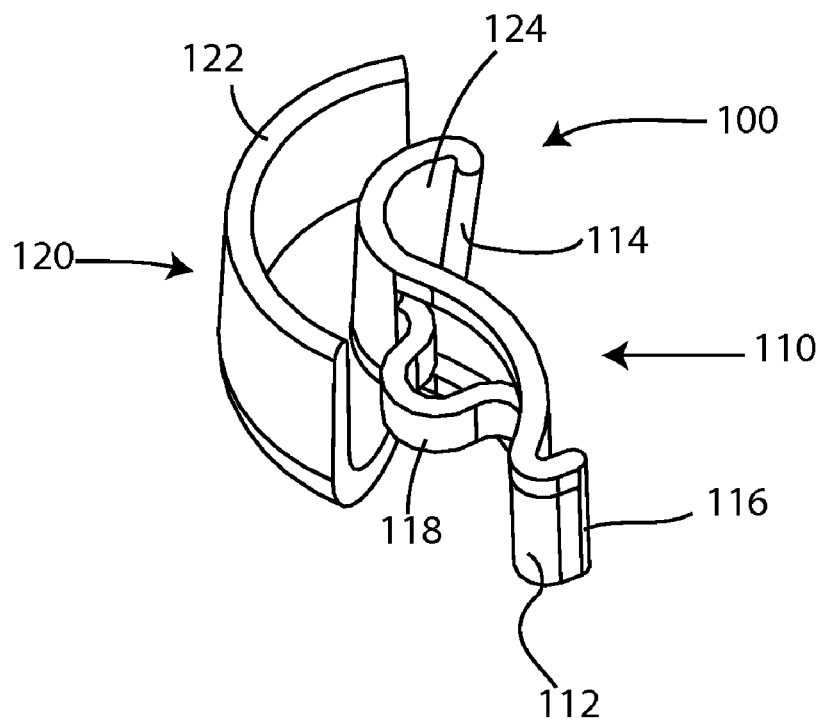
FIG. 3A is a perspective view of the implant of FIG. 2, in an open configuration.
Figure 3B:
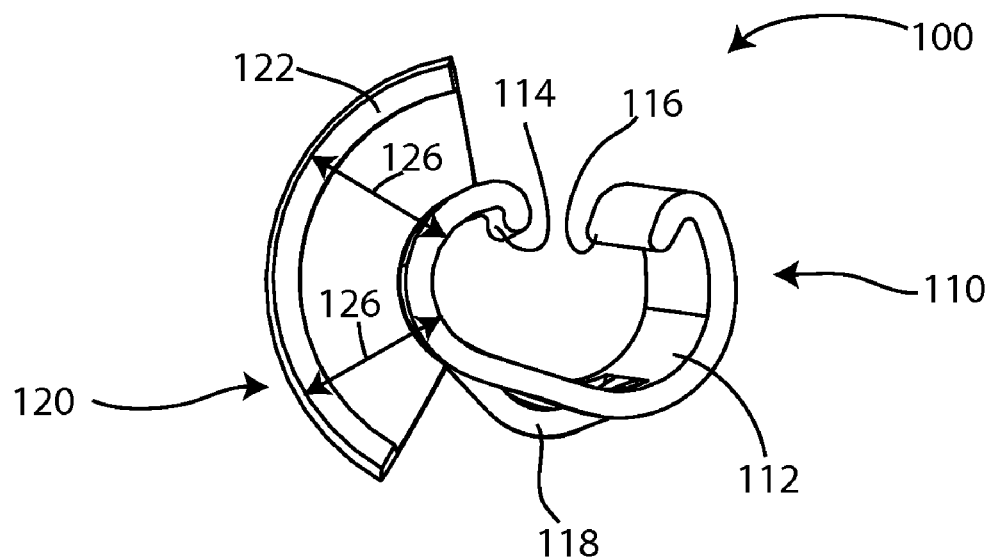
FIG. 3B is a perspective view of the implant of FIG. 2 in a closed configuration.

A portion of the collar 112 comprises a spring member 118. As seen in FIG. 3A, when the spring member 118 is in one shape, the bracket 110 is at a first stable low energy configuration, in which the collar is "open" and the ends 114, 116 are spaced relatively far apart. As seen in FIG. 3B, when the spring member 118 is in a second shape, the bracket 110 is at a second stable low energy configuration, in which the collar is "closed" and the ends 114, 116 are spaced relatively closer together. The bracket 110 is reversibly transformable, meaning it is transformable from the first configuration to the second configuration and from the second configuration to the first configuration. Transformation may be attained by positioning the bracket: for example, pushing the "open" bracket against the side of the spinous process may move the spring member 118 from the first shape to the second shape, transforming the bracket from the first open configuration to the second closed configuration. Transformation may also be attained by pushing the bracket toward the second configuration. This transformation may be similar to that found in a common hair barrette which snaps from a first open configuration to a second closed configuration when pressed against a surface. When the bracket 110 is closed around the spinous process in the second low energy configuration, such as in FIG. 2, the bracket substantially encircles the spinous process and the spacer 120 is retained by the spinous process and held in a stable position relative to the spinous process. A stable position is one in which a micro amount of relative motion may be possible, but not gross migration of the spacer. Transformation of the bracket from the open configuration to the closed, and vice versa, may be referred to as toggling, where toggling is defined as moving between the two different stable low-energy configurations. Toggling of the bracket between configurations may take place in situ, after the spacer has been placed between the spinous processes.

Bracket 110 may be described as bi-stable, meaning that it can attain two different stable low-energy configurations. A low-energy configuration is a configuration in which a relative local minimum of energy is stored. Energy types may includes kinetic, thermal, resilient or any other type of energy. Bracket 110 stores resilient energy, which may be also called stored spring force.

Implants with a bracket 110 fixation portion may be inserted unilaterally. From either lateral approach, an opening is created to access the spinous process gap at the targeted vertebral level, between an inferior spinous process of one vertebra and the superior spinous process of the adjacent second vertebra. The spacer and superior end of the bracket are inserted into the gap, and the spacer is moved to a desired orientation relative to the spine. The desired orientation may be between the inferior and superior spinous processes. The bracket is rotated toward the inferior spinous process, and positioned against the inferior spinous process. The bracket is urged against the inferior spinous process until the bracket snaps closed around the inferior spinous process. When the bracket is thus coupled to the inferior spinous process, the spacer is oriented toward the superior spinous process, and superior to the bracket, as seen in FIG. 2.

The spacer of the implant may be formed and shaped in a variety of ways. In the embodiment depicted in FIGS. 2 and 3, the spacer 120 has a regular arcuate shape and is hollow and open posteriorly. An outer wall 122 forms the superior side of the spacer, and an inner wall 124 forms the inferior side of the spacer. As seen in FIG. 3B, a radial dimension 126, measured normal to the curve of the outer wall 122, is substantially constant between the outer wall 122 and the inferior spinous process 36. The radial dimension 126 may also be called a spacer offset dimension. During extension, the superior spinous process 56 may contact the outer wall 122 and urge the outer wall 122 toward the inner wall 124. As the distance between the walls 122, 124 grows shorter, progressive resistance may occur, in which increasing force is required to move an additional distance. When the outer wall 122 contacts the inner wall 124 and the inner wall 124 contacts the inferior spinous process 36, an extension stop occurs, wherein extension is physically limited by the contact between the walls and the process, and can proceed no further. The spacer 120 may also be configured to be compliant, or resilient, providing variable resistive force which urges the superior and inferior spinous processes apart in response to extension of the spine.

The regular arcuate shape of the spacer provides a constant spacer offset dimension between the spinous processes 36, 56 regardless of their relative orientation through a range of motion. In addition, a uniform extension stop may be provided, in which the stop occurs at the same distance between the spinous processes regardless of the relative orientation of the spinous process. Therefore, even as a patient bends laterally during extension, thus changing the relative orientation of the spinous processes, a constant spacer offset dimension is provided and a uniform extension stop at that vertebral level. The spacer maintains a minimum distance between the adjacent spinous processes at that level.

A uniform extension stop is a stop or spacer which provides substantially the same separation between adjacent spinous processes, regardless of the relative orientation of the spinous processes due, for example, to the patient's posture at any given moment. For example, the patient's spine could be in extension combined with axial or lateral rotation. The 3D profile or surface of a uniform extension stop could be created, for example, by offsetting the 3D surface of one of the spinous processes by a constant dimension so that each point on the original surface translates along a vector normal to the surface at that point. This method could also be used with an approximate surface composed of numerous small triangular facets, where each facet is offset by a constant dimension along its normal vector, and all the resulting facets are trimmed with respect to each other. The approximation could be carried further by creating a small set of original surfaces that encompasses the morphological variances seen in a larger set of anatomic data from, for instance, CT scans of real patients. The set of original surfaces would then be uniformly offset as described above. Contemporary 3D CAD software is adept at this sort of transformation. Approximation of many individual surfaces down to a small set of sizes remains in the spirit of uniformity, since it is common practice to generate a size range in many products, from hip stems to jeans. The end result would be a family of spacers which vary by internal configuration (several sizes to provide a close fit to the spinous process) and by spacer dimension (several sizes to provide the necessary amount of separation between spinous processes).

FIGS. 4-7 illustrate additional embodiments of interspinous spacer implants comprising the bracket 110 and a spacer. The embodiments described may be implanted as illustrated in FIG. 2, in which the spacer is positioned on the superior side of the bracket 110. However, it is appreciated that, alternatively, the spacers may be shaped and configured to be positioned on the inferior side of the bracket 110, and therefore be positioned on the inferior side of a superior spinous process 56 adjacent to an inferior spinous process 36.

Figure 4:
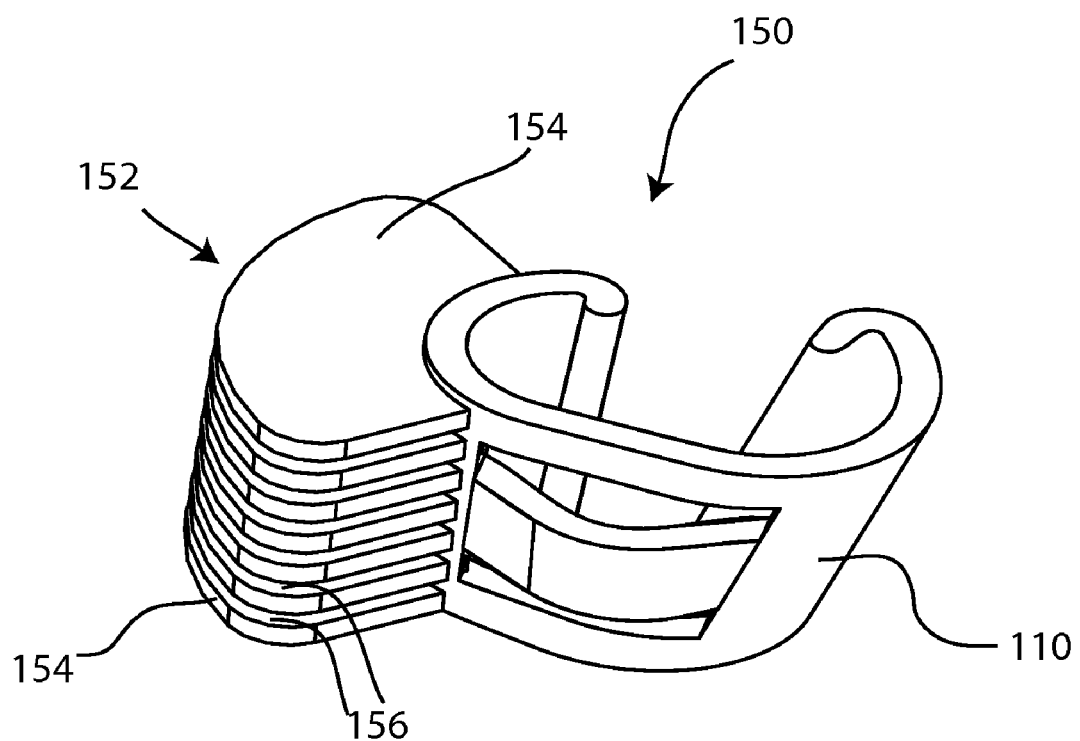
FIG. 4 is a perspective view of an alternative embodiment of an interspinous spacer implant.

Referring to FIG. 4, an alternative embodiment of an implant comprising the bracket and an alternative spacer is shown. Implant 150 includes the bracket 110, which is coupled to a spacer 152. Spacer 152 also has a regular, arcuate shape, and is formed of a series of resilient plate-like flanges 154 interleaved with gaps 156. When the bracket 110 is coupled to an inferior spinous process as in the method set forth previously, the flanges 154 extend substantially perpendicular to the spinous process. During extension, as the superior spinous process contacts and deforms the spacer 152, the flanges 154 sequentially deflect, providing compliant resistance, which may nonlinearly increase as extension continues. This configuration may provide a uniform extension stop with a constant spacer offset dimension.

Figure 5:
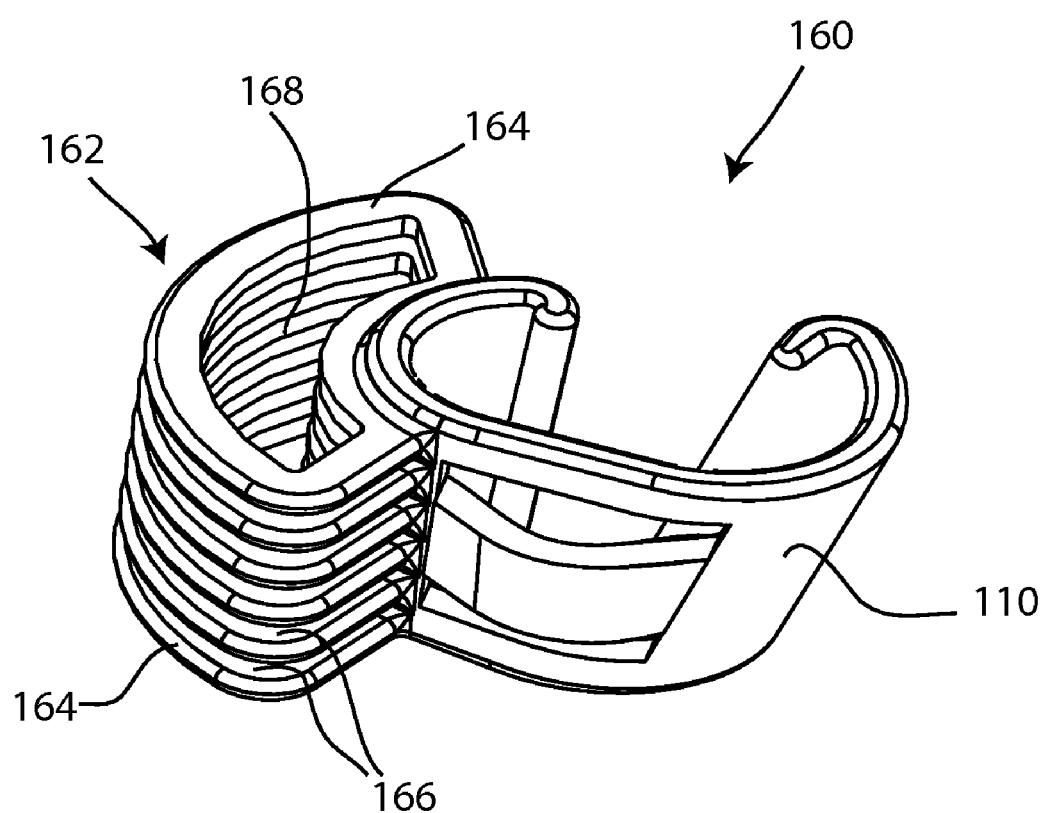
FIG. 5 is a perspective view of an alternative embodiment of an interspinous spacer implant.

Referring to FIG. 5, another alternative embodiment of an implant comprising the bracket and an alternative spacer is shown. Implant 160 includes the bracket 110, which is joined to a spacer 162. Spacer 162 has a regular, arcuate shape, and is formed of a series of flanges 164 interleaved with gaps 166. The flanges 164 are not plate-like but have a central cut-out 168 so that the spacer 162 is hollow and open both anteriorly and posteriorly. During extension, as the superior spinous process contacts and deforms the spacer 162, the flanges 164 sequentially deflect, providing soft resistance, which may nonlinearly increase as extension continues. This configuration may provide a uniform extension stop with a constant spacer offset dimension. Implants 150 and 160 may include flange designs that are optimized to provide desired flexibility and a definite endpoint or extension stop.

Figure 6:
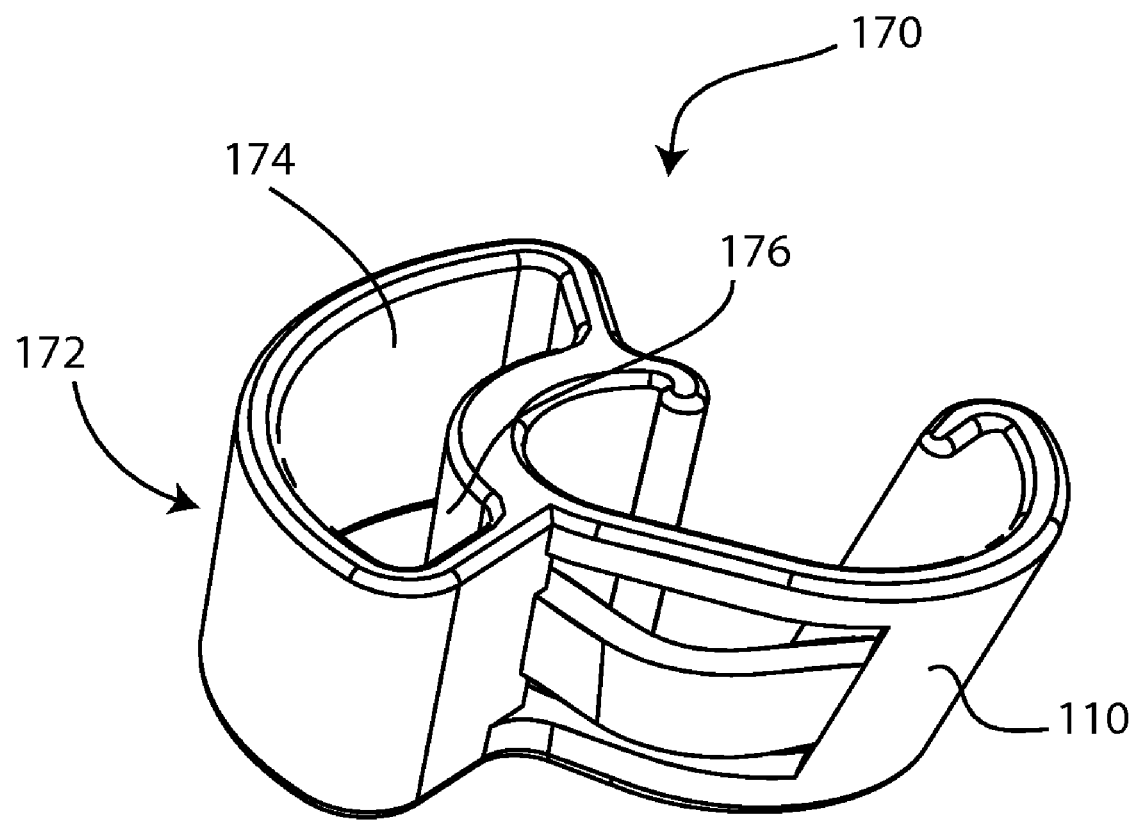
FIG. 6 is a perspective view of an alternative embodiment of an interspinous spacer implant.

Referring to FIG. 6, yet another alternative embodiment of an implant comprising the bracket and an alternative spacer is shown. Implant 170 includes the bracket 110, which is joined to a spacer 172. Spacer 172 is similar in configuration to spacer 120, except that spacer 172 is open both anteriorly and posteriorly, forming a closed loop shape. This configuration may provide levels of flexibility and resilience that differ from other embodiments.

Implants 100, 150, 160, and 170 are each shaped so that each may provide a constant spacer offset dimension, and a uniform extension stop. The spacer offset dimension may vary, and may be tailored to replicate normal human physiological biomechanics. Additionally, a medial-lateral width of the spacer may be variable to accommodate the expected range of motion of adjacent spinous processes.

Figure 7:
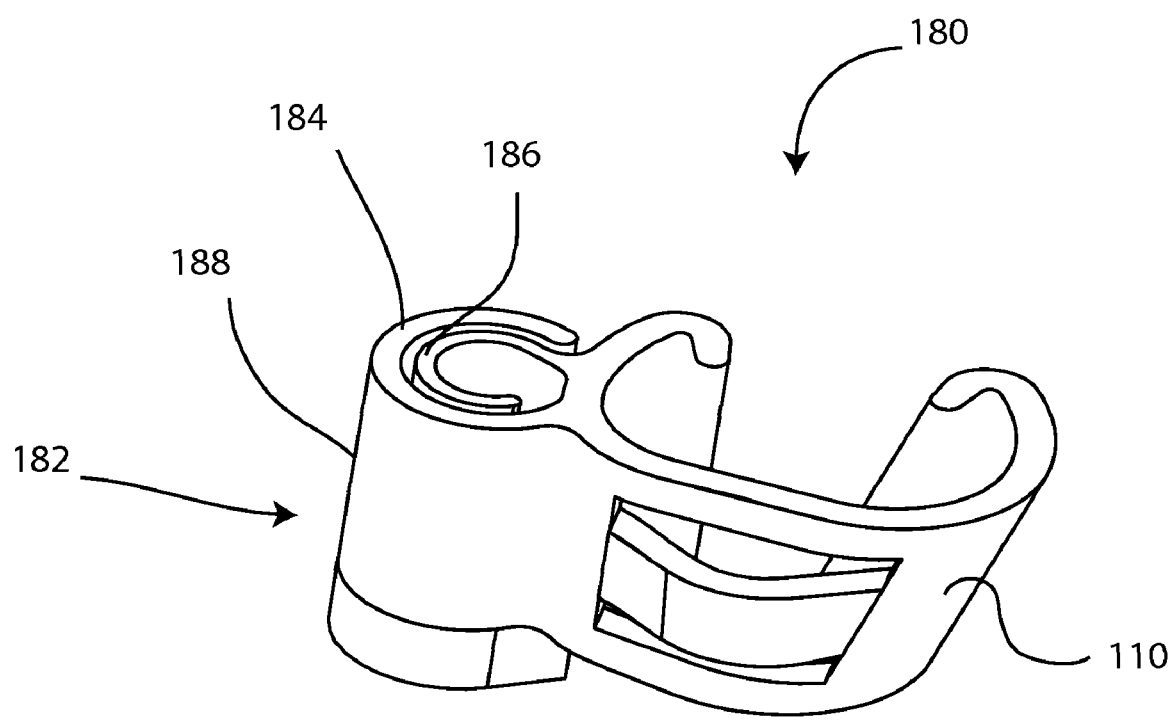
FIG. 7 is a perspective view of an alternative embodiment of an interspinous spacer implant.

Referring to FIG. 7, yet another alternative embodiment of an implant comprising the bracket and an alternative spacer is shown. Implant 180 includes the bracket 110, which is joined to a spacer 182. Spacer 182 comprises concentrically arranged semi-cylindrical flanges, including outer flange 184 and inner flange 186. Although two flanges are included in this embodiment, alternative implants may comprise one semi-cylindrical flange, or several, arranged concentrically. The flanges 184, 186 are positioned such than an exterior wall 188 of the semi-cylinder formed by the flanges extends antero-posteriorly when the implant is secured to a vertebra. An anterior-posterior height of the spacer 182 may exceed a medial-lateral width of the spacer member. During extension, the superior spinous process may contact the outer flange 184, which deflects and may eventually contact inner flange 186, providing a nonlinear increase in resilient force. Implant 180 may provide flexibility, and a uniform extension stop.

Figure 8A:
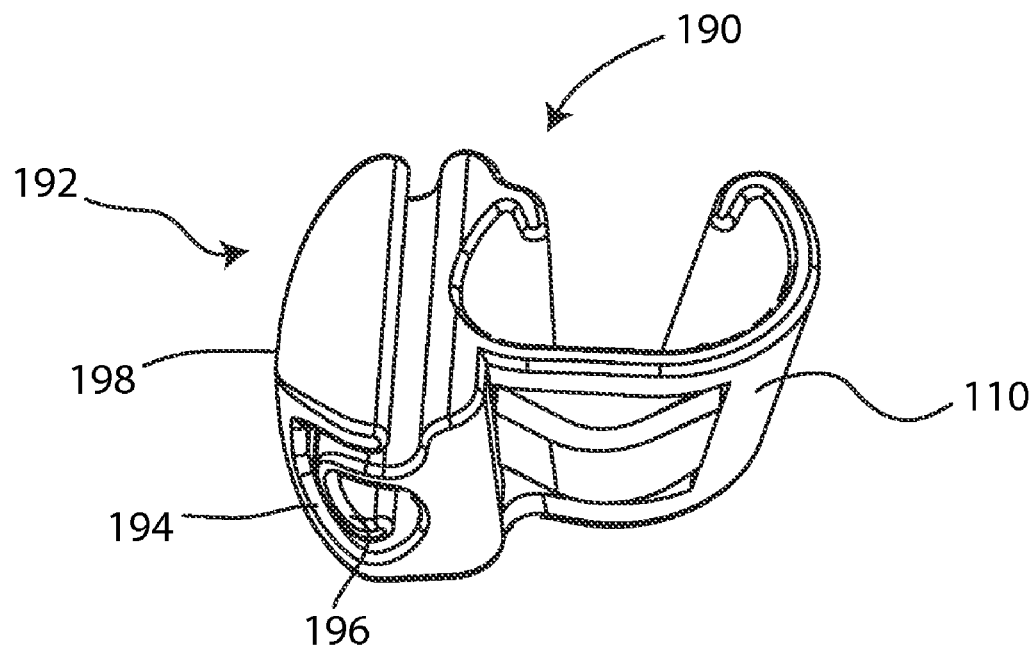
FIG. 8A is a perspective view of an alternative embodiment of an interspinous spacer implant.
Figure 8B:
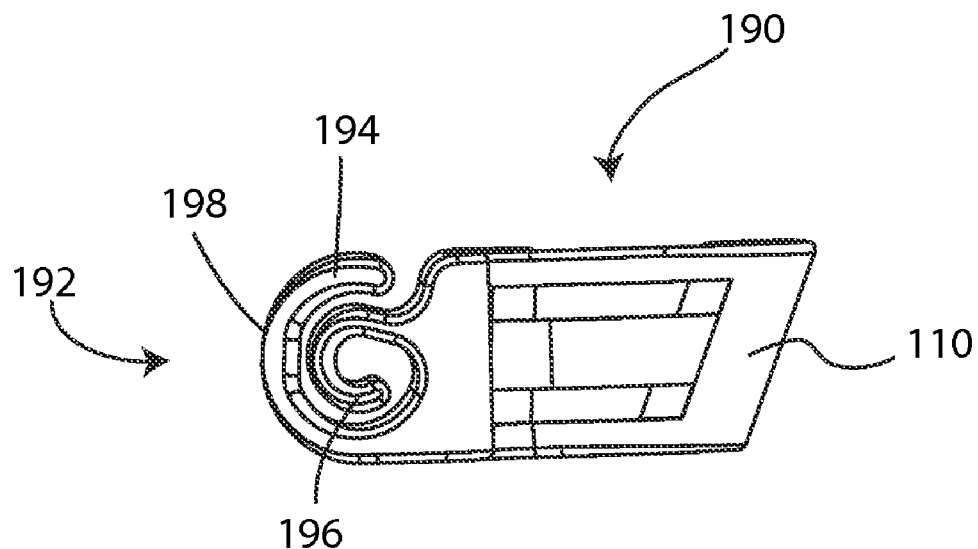
FIG. 8B is a lateral view of the implant of FIG. 8A.

Referring to FIGS. 8A and 8B, another alternative embodiment of an implant comprising the bracket and an alternative spacer is shown. Implant 190 includes the bracket 110, which is joined to a spacer 192. Similar to implant 180, spacer 192 comprises concentrically arranged semi-cylindrical flanges, including outer flange 194 and inner flange 196. However, in this embodiment the flanges 194, 196 are positioned such than an exterior wall 198 of the semi-cylinder formed by the flanges extends medial-laterally when the implant is secured to a vertebra. A medial-lateral width of the spacer 192 may exceed an anterior-posterior height of the spacer member. During extension, the superior spinous process may contact the outer flange 194, which deflects and may eventually contact inner flange 196, providing a nonlinear increase in resilient force. Implant 190 may provide flexibility, and a uniform extension stop.

Figure 9:
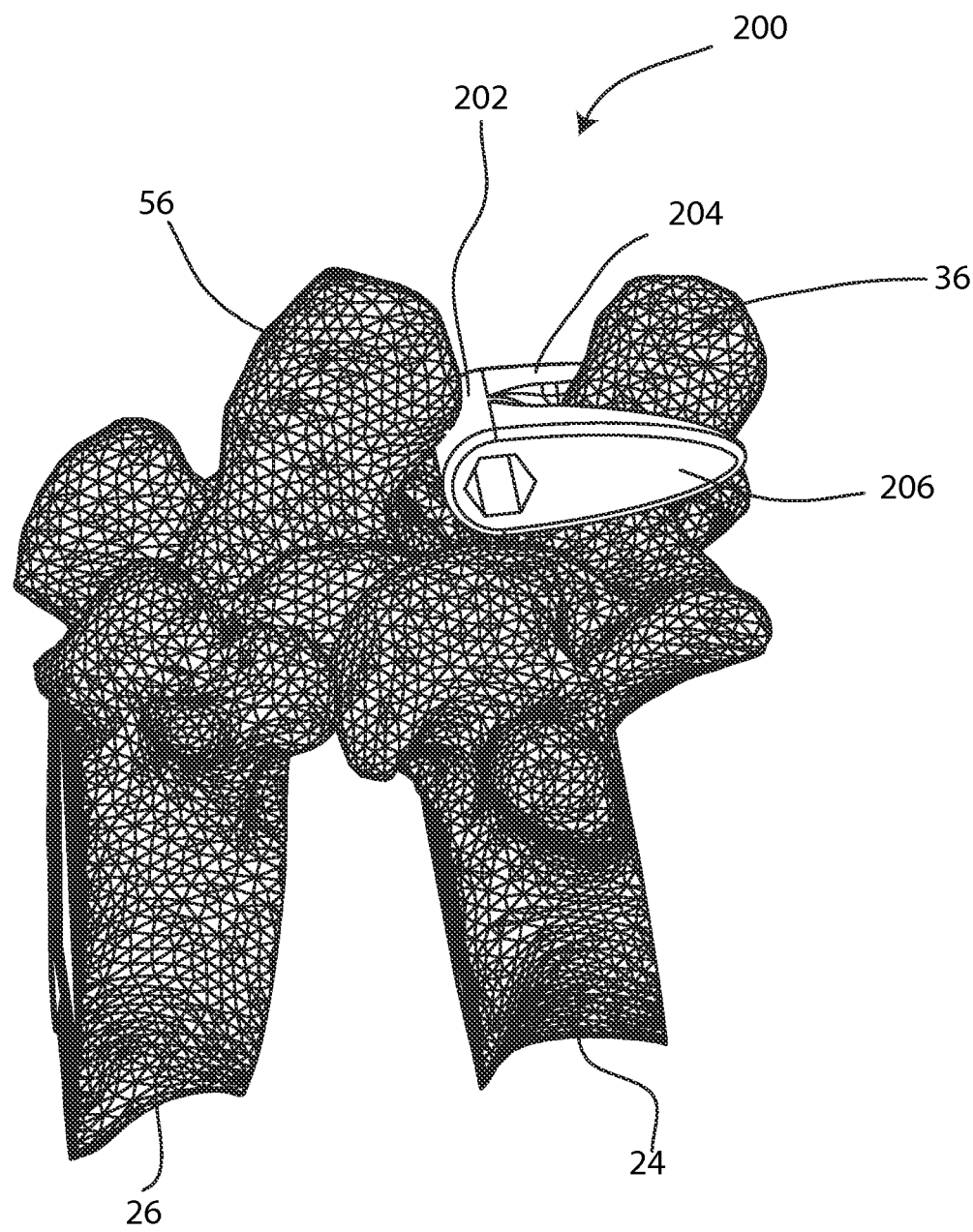
FIG. 9 is a lateral perspective view of an interspinous spacer implant implanted between two vertebrae in a portion of a spine.

Referring to FIG. 9, a perspective view illustrates one embodiment of an implant 200, which may be termed an interspinous spacer, implanted between two adjacent vertebrae 24, 26. Implant 200 comprises a spacer 202 and a fixation portion comprising two flanges 204, 206. When implanted between two vertebrae 24, 26 and positioned to a desired orientation, the two flanges 204, 206 may engage opposite lateral sides of the inferior spinous process 36, to secure and retain the spacer relative to the spinous process. The implant remains in its implanted location through the full range of spinal motion.

Figure 10A:
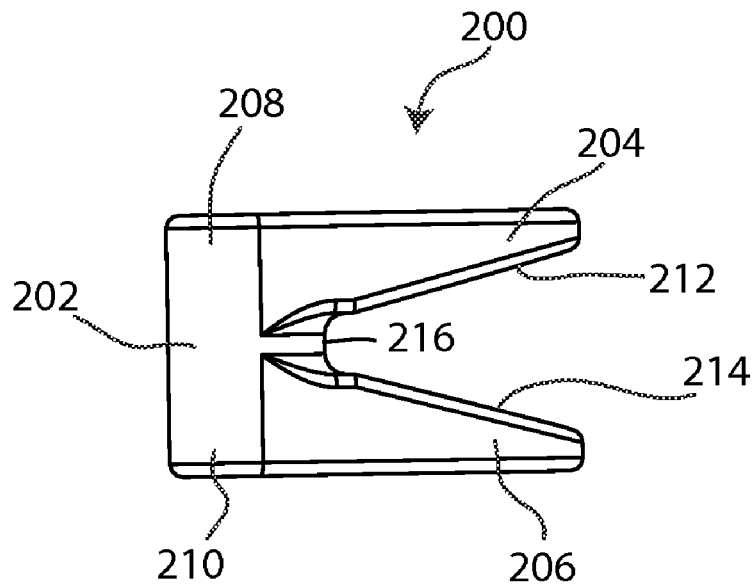
FIG. 10A is a posterior view of the implant of FIG. 9.
Figure 10B:
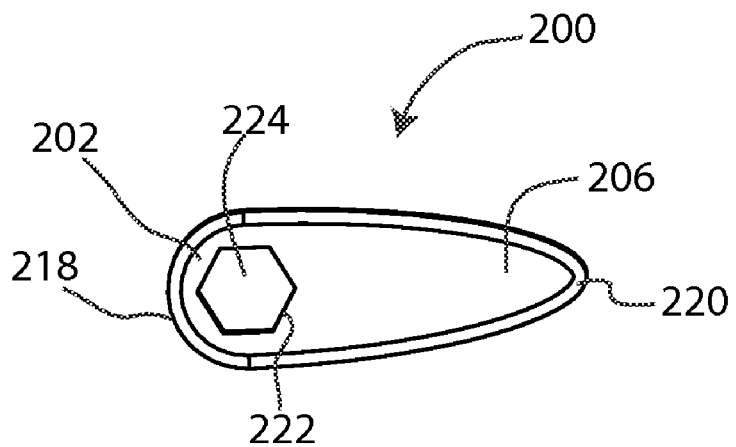
FIG. 10B is a lateral view of the implant of FIG. 9.

FIG. 10A is an anterior view of implant 200, and FIG. 10B is a lateral view of one lateral side of the implant. Referring to FIG. 10A, spacer 202 has a first end 208 from which flange 204 extends orthogonally, and a second end 210 from which flange 206 extends orthogonally. Flange 204 has an inner wall 212, and flange 206 has an inner wall 214, and the two inner walls 212, 214 are angled so that the flanges taper and the implant forms an approximate "V" shape. The inner walls 212, 214 converge at a saddle 216. The angles of the inner walls 212, 214, and the shape of the saddle 216 may vary, so that variations in size and profile of different spinous processes may be accommodated. Similarly, the lengths of the flanges, and width of the spacer may vary. The spacer may comprise a compliant, resilient material, or a rigid material, or may comprise a layered configuration with compliant materials layered over rigid elements.

As seen in FIG. 10B, a lateral profile of the implant resembles a smooth exaggerated egg shape, with the flanges tapering in height from a cephalad end 218 to a caudal end 220. Implant 200 may be monolithic, and may be bilaterally symmetrical, in this instance meaning it is symmetrical on either side of the sagittal plane. An insertion feature 222 is near the cephalad end 218. In this embodiment of the invention the insertion feature 222 is hexagonally shaped, to accommodate a hexagonal driver. However, the insertion feature could have any shape in place of hexagonal, such as square, hexalobular, oval, or paired holes. In addition, the insertion feature could be internal as shown, or external, or could extend along the outer surface of the flange if necessary. The insertion feature may be located only on one side of an implant, or on both sides.

Figure 11:
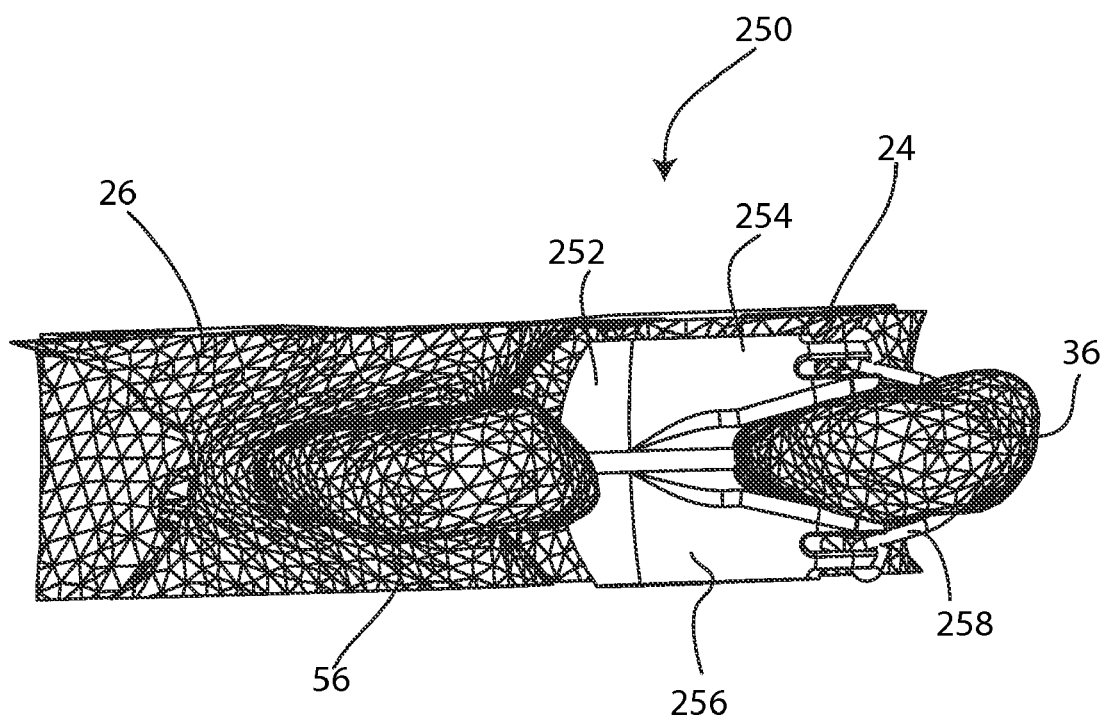
FIG. 11 is a posterior view of an embodiment of an interspinous spacer implant with a tether, implanted between two vertebrae in a portion of a spine.

The insertion feature 222 opens into a hollow 224 which extends the length of the spacer 202. This hollow spacer allows for intrinsic spring action when, during extension, the superior spinous process pushes against the spacer member 202. Non-linearly increasing resistance, and a definite extension limit with a minimum separation, may be provided by implant 200. Implant 200 may also provide a variable extension stop Referring to FIG. 11, an anterior view alternative embodiment of an interspinous implant with an optional tether is illustrated, implanted between two vertebrae 24, 26. Implant 250 is generally "V" shaped and comprises a spacer 252 and a fixation portion comprising two flanges 254, 256. Flanges 254, 256 are shaped to engage the opposite lateral sides of the spinous process 36, to retain the spacer relative to the spinous process. A tether 258 is connected to flange 256, extends around spinous process 36, and is connected on the far lateral side to flange 254. Together, the tether, flanges and spacer fully encircle the inferior spinous process 36. Similar to implant 200, implant 250 may be bilaterally symmetrical.

Figure 12:
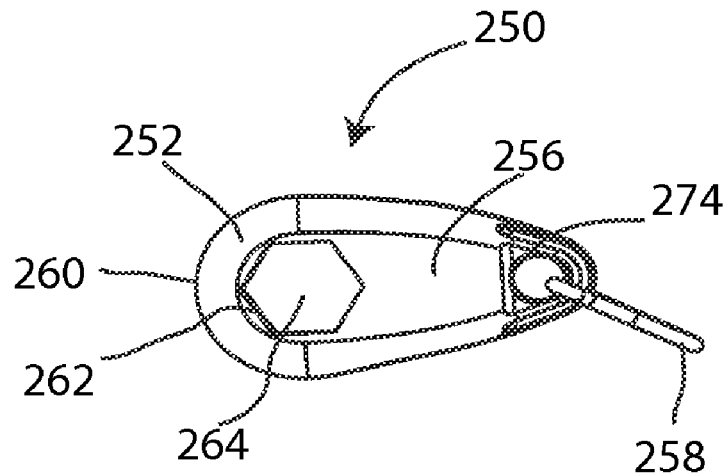
FIG. 12A is a lateral view of the implant of FIG. 11.
FIG. 12B is a posterior view of the implant of FIG. 11.
Figure 12B:
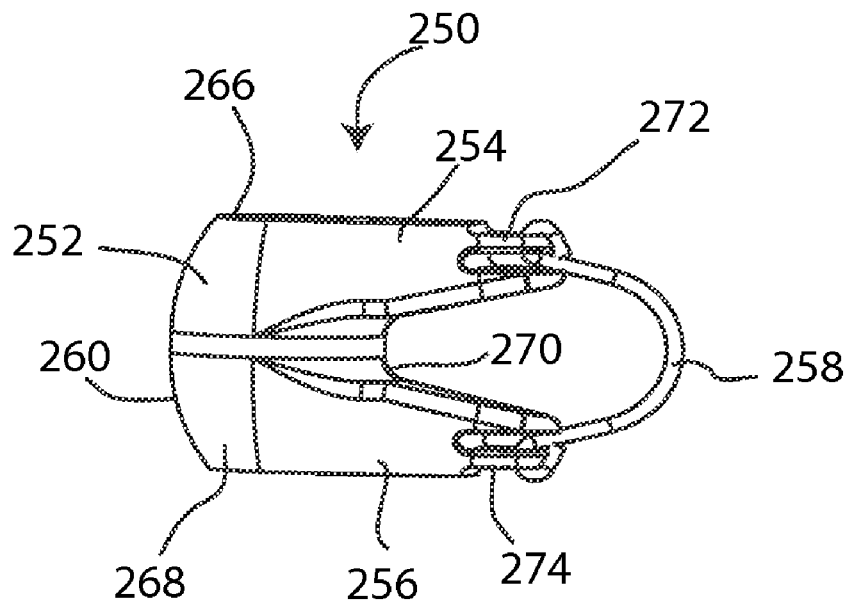

Referring to FIGS. 12A and 12B, lateral and posterior views of implant 250 and tether 258 are shown. From the lateral perspective, implant 250 has an elongated egg shape. The spacer 252 has a substantially arcuate shape with a rounded superior wall 260 and an insertion feature 262 which opens into a hollow 264. In this embodiment, a first end 266 and a second end 268 of the spacer 252 have flat lateral surfaces, but in other embodiments those surfaces may be rounded. The flanges 254, 256 extend orthogonally from the spacer 252, and taper both in height and width. The flanges 254, 256 converge at a saddle 270, which may be contoured to accommodate the superior profile of an inferior spinous process. The saddle and flanges may be sized and shaped for a preferred fit between the flanges and the spinous process to limit lateral movement of the spacer and to retain the implant relative to the inferior spinous process. The flanges may be of any length. The lateral profile shape of the implant could be as depicted, or could be oval, paisley-shaped, or kidney-shaped, among others. The hollow configuration of the spacer may provide intrinsic resilient spring action during extension, and the rounded superior wall of the spacer may provide a minimum separation distance between the spinous processes and a uniform extension stop. The configuration of the spacer may also provide variable resistive force urging the inferior and superior spinous processes apart in response to extension of the spine.

At tapered end of flange 254 is located a tether attachment feature 272, and at the end of flange 256 is tether attachment feature 274. Attachment features 272, 274 each comprise an opening through which a tether may pass. Once passed through an attachment feature 272, 274, the tether may be secured, either to the implant 250, or to itself to form a continuous loop. Methods of securing the tether may include tying a surgical knot or knots, crimping a fastener to the tether, or using a securing device such as a knotless line lock, among others. The combination of flanges and tether(s) secures the spacer to one of the spinous processes, snugly or loosely as appropriate. Thus the spacer stays in its installed location in extension, due to the pinching action of the spinous processes against the central spacer portion and the action of the flanges against the sides of the spinous process. It also stays in place in flexion due to the action of the tether around one of the spinous processes.

Figure 13A:
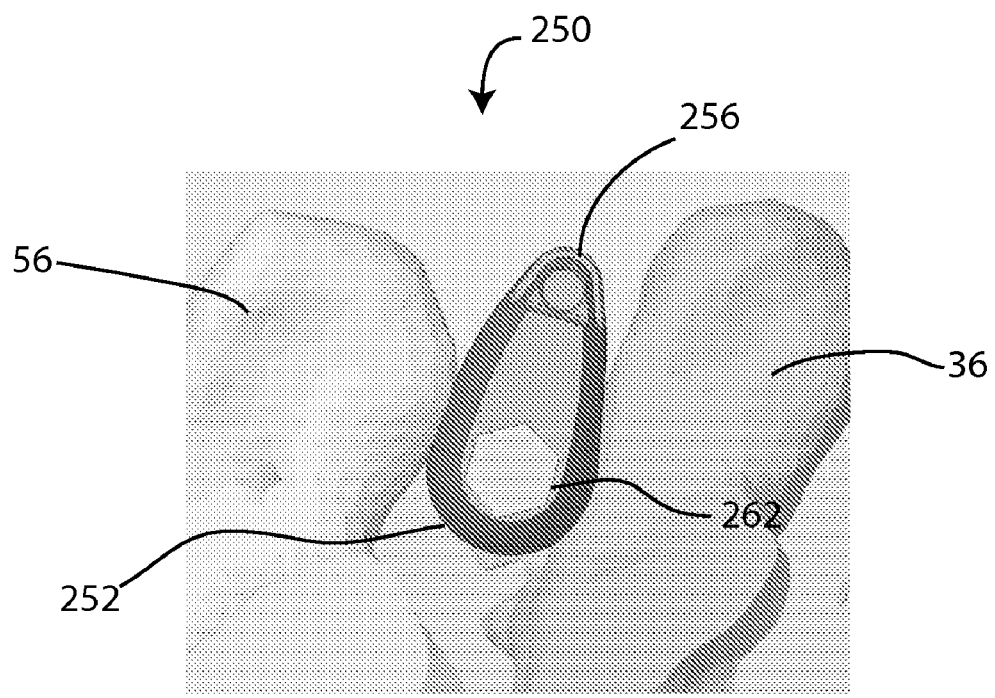
FIG. 13A is a lateral view of the implant of FIG. 11 in an anterior-posterior orientation in an interspinous gap between two spinous processes.
Figure 13B:
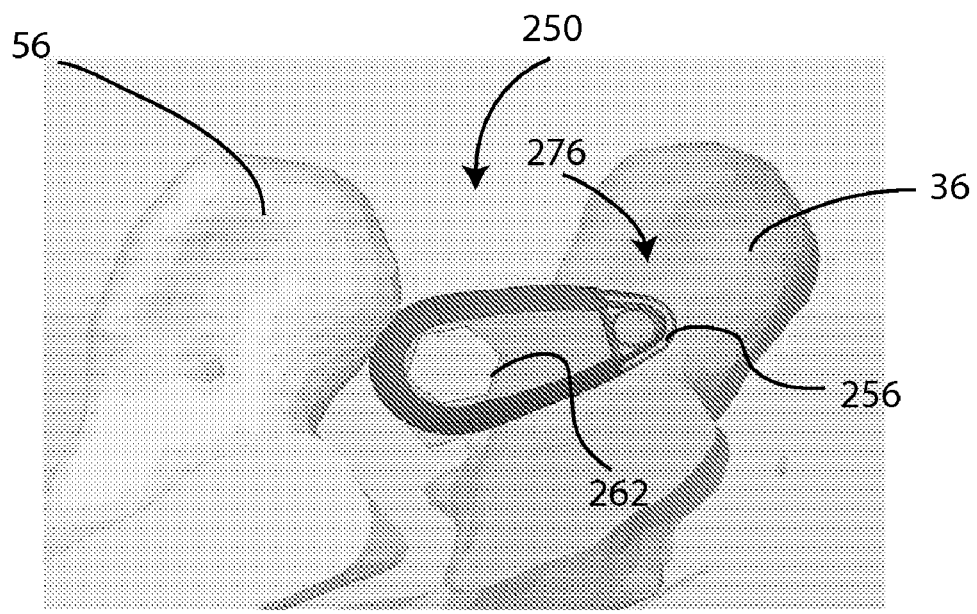
FIG. 13B is a lateral view of the implant of FIG. 11 in a cephalad-caudal orientation.

FIGS. 13A and 13B illustrate one method for the insertion and positioning of implant 250. It is appreciated that other implants described herein with similar shapes, such as implants 200, 280 and 420-470 may be inserted and positioned in a similar manner. Implant 250 may be inserted unilaterally from the right or left side of the spinous processes, and does not require disruption of the supraspinous ligament. The implant is inserted medially into the interspinous process gap in an anterior-posterior orientation, with the spacer 252 anteriormost and the tips of the flanges 254, 256 posteriormost, as seen in FIG. 13A. Once the spacer 252 has reached a desired medial-lateral location in the interspinous process gap with the saddle lined up with the spinous processes, the spacer 252 is rotated in the direction of the arrow 276 until the flanges reach a desired position on either side of the inferior spinous process 36, seen in FIG. 13B. The torque to rotate the spacer 252 may be provided by an instrument (not shown) configured to mate with insertion feature 262, or may be provided by simply pushing the accessible flange in the direction of arrow 276. Since both flanges are orthogonal to the spacer member and parallel to one another, they will move simultaneously on opposite sides of the spinous process as the spacer is rotated. It is appreciated that, if desired, the spacer could be rotated in an anterior-cephalad direction until the flanges reach positions on either side of the superior spinous process 56.

Other methods of implantation and positioning may be used. For example, if the lateral length of the implant, from the superior wall 260 to the tips of the flanges, exceeded the anterior-posterior dimension of the interspinous gap, an alternative implantation method could be implemented. The implant could be inserted obliquely until its flange ends bracket the supraspinous ligament, then rotated about the supraspinous ligament in the transverse plane until the spacer rests between the spinous processes. Then the implant could be rotated about the spacer in the sagittal plant until the flanges rest beside one of the spinous processes.

The tether 258 may comprise commercial suture, such as #2 or #5 braided polyester suture, a broad, flat braided tape, surgical cable or wire, or any flexible strand. The tether may be connected to one or both flanges prior to implantation, or connected to one flange and passed through the opposite tether attachment feature, or not connected to the implant at all prior to implantation. Connection to the flanges may be through knotting, crimping, gluing, over-molding, insert molding, or the tether may be formed from implant substrate material. The tether may be secured to itself, to one or both attachment features, or to a separate attachment component such as a suture clip. A second tether may be included and secured around the superior spinous process, if desired. Use of one tether may assist in retaining the implant. Addition of a second tether may provide motion restriction when the patient moves into forward flexion.

The tether may be positioned around the spinous process by means of a cannulated instrument resembling a shepherd's crook. The tether may be pre-loaded in the crook, or passed through the crook after the crook is positioned. The crook may be positioned around the spinous process and the tether delivered through the crook. A first end of the tether may be connected to one flange of the implant, and the implant inserted or pushed into the interspinous gap while simultaneously, the tether is pulled back through the crook, helping to pull the implant into the interspinous gap. After the implant is in its desired position in the interspinous gap, and rotated so that the flanges are on either side of the spinous process such as in FIG. 13B, the free or second end of the tether may be connected to the other, accessible flange. Alternately, a shaped suture grasper could be used to place the tether.

Figure 14:
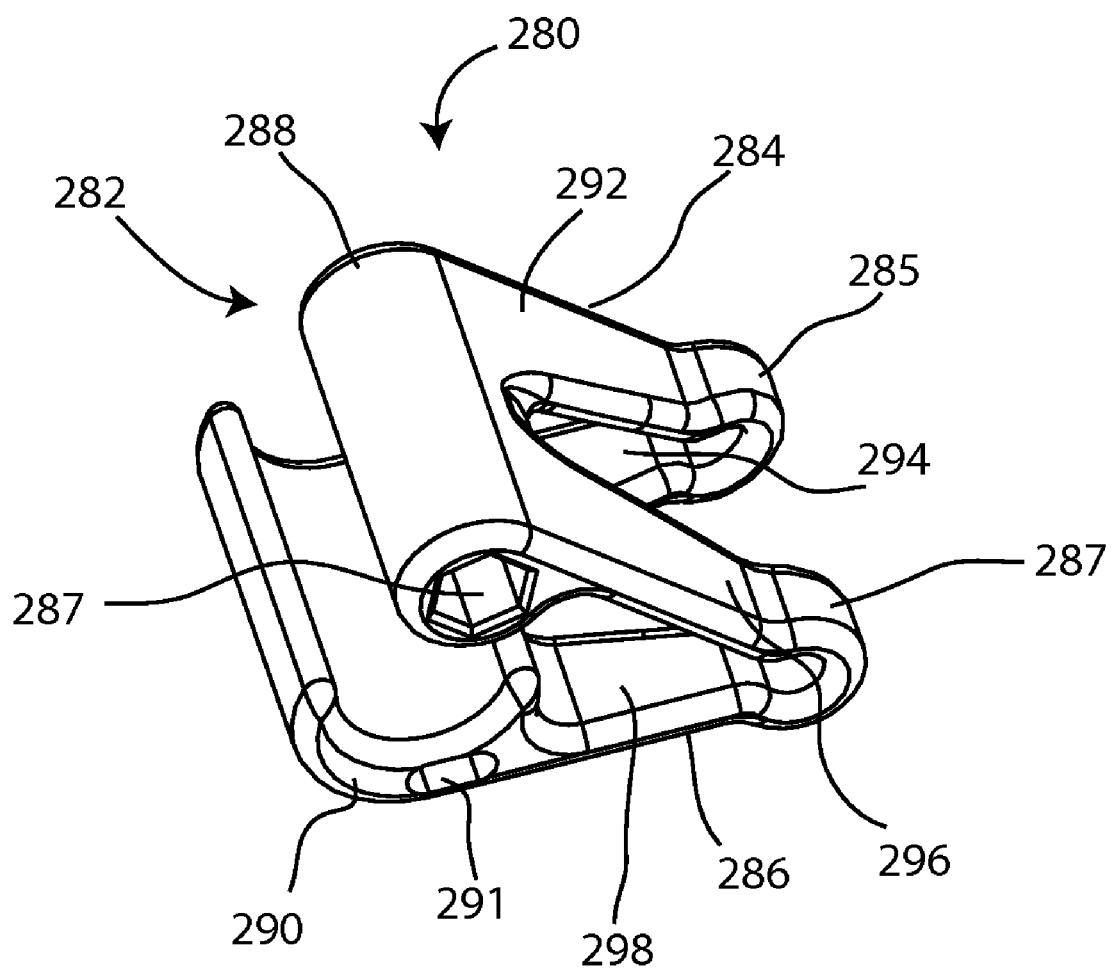
FIG. 14 is a perspective view of an alternative embodiment of an interspinous spacer implant in an open configuration.

Referring to FIG. 14, a perspective view shows an implant 280. Implant 280 comprises a spacer 282, and two flanges 284, 286 which are coupled to the spacer in a substantially orthogonal orientation, similar to the V-shaped configuration of implants 200 and 250. A portion of spacer 282 may be expanded in the anterior-posterior orientation to restrict rotation of the spacer out of a desired orientation relative to the spine. The expanded spacer may also provide resilient resistance between the spinous processes during extension.

Figure 15A:
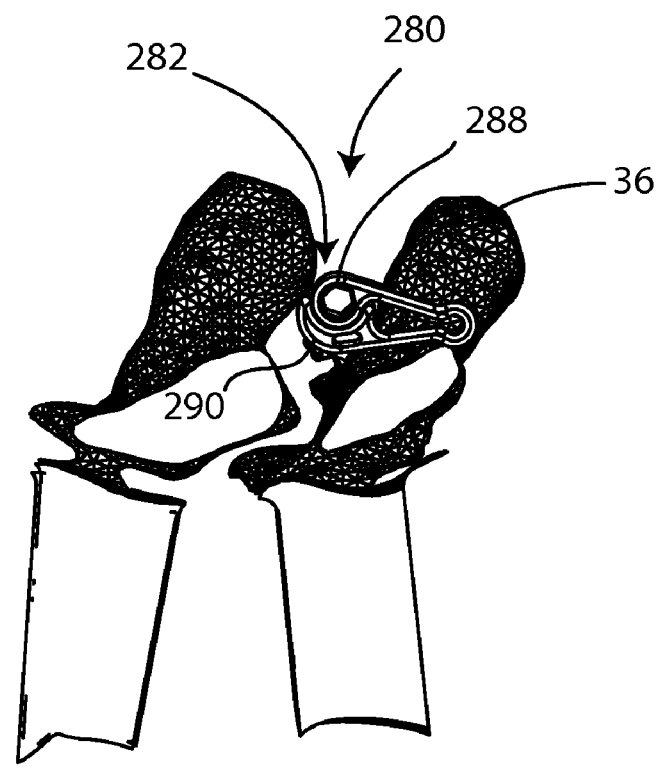
FIG. 15A is a lateral view of the implant of FIG. 14 implanted between two vertebrae in a portion of a spine and in a closed configuration; and 15B is a lateral view of the implant of FIG. 15A in an open configuration.
Figure 15B:
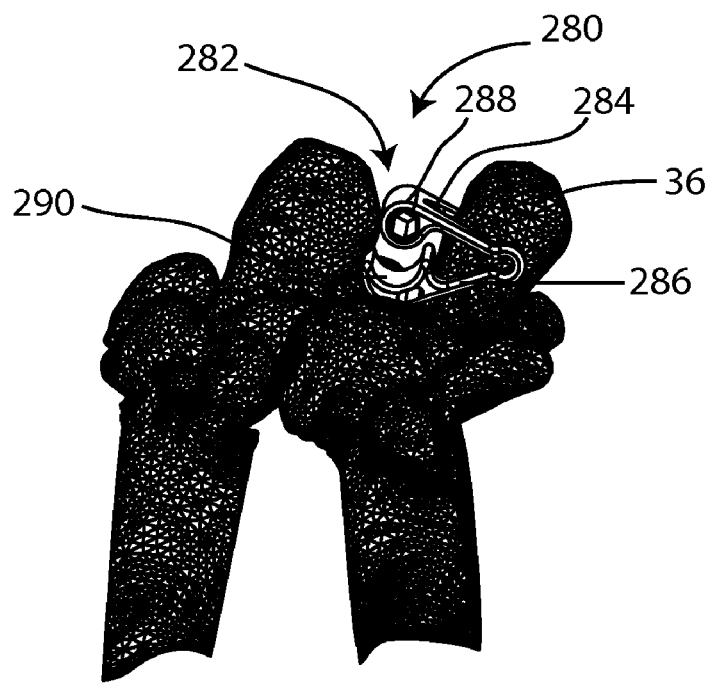

Spacer 282 comprises a first spacer member 288 and a second spacer member 290. Spacer member 288 may be substantially hollow, and has an insertion feature 287. Spacer member 290 is shaped to mate with spacer member 288, and has an insertion feature 291. Spacer members 288 and 290 may be configured to fit together such that when held together they are sized to fit into the interspinous gap. After insertion, the implant 280 may be rotated until the flanges 284, 286 reach a desired position on either side of the spinous process 36, as seen in FIG. 15A. Once so positioned, the spacer members 288 and 290 may be released and allowed to expand in the anterior-posterior plane, as seen in FIG. 15B. During expansion, one or both of the spacer members 288, 290 may move.

Returning to FIG. 14, each flange 284, 286 is substantially V-shaped. Flange 284 comprises a posterior strut 292 and an anterior strut 294 which are joined at an elbow 285. Similarly, flange 286 comprises a posterior strut 296 and an anterior strut 298 joined at an elbow 287. The flanges 284, 286 each have intrinsic spring action, such that if posterior strut 292 and anterior strut 294 (or posterior strut 296 and anterior strut 298) are held together then released, the flange will spring back to the low energy point V shape. Spacer member 288 is coupled to and extends between the posterior struts 292, 296. Spacer member 290 is coupled to and extends between the anterior struts 294, 298. Consequently, spacer members 288, 290 may be held together in a closed position. When released, they will intrinsically move into an open position.

Spacer 280 may be unilaterally inserted between the spinous processes and rotated in a manner similar to that described for implant 250 and depicted in FIGS. 13A and 13B. An insertion tool or tools (not shown) may engage in insertion features 287, 291, and pinch the spacer members 288, 290 together. The implant 280 is fit into the interspinous gap with the spacer 282 oriented anteriormost and the elbows 285, 287 of the flanges posteriormost. Once the implant 280 reaches a desired medial-lateral orientation, it may be rotated until the flanges 284, 286 are in a desired position on either side of spinous process 36. At this point, the tool may be disengaged, or the spacer members otherwise released, from the spacer, allowing the spacer to expand in the anterior-posterior plane to attain the open position. The spacer may provide compliant, resilient resistance as the distance between the spinous processes decreases during extension, and a uniform extension stop at a minimum separation distance. Optionally, a tether may cooperate with the flanges or the hollow spacer member to retain the implant relative to a spinous process.

Figure 16A:
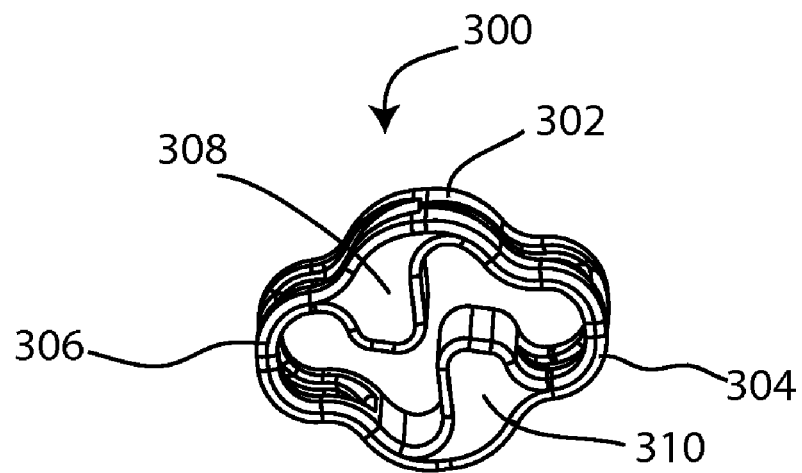
FIG. 16A is a lateral perspective view of an alternative embodiment of an interspinous spacer implant.
Figure 16B:
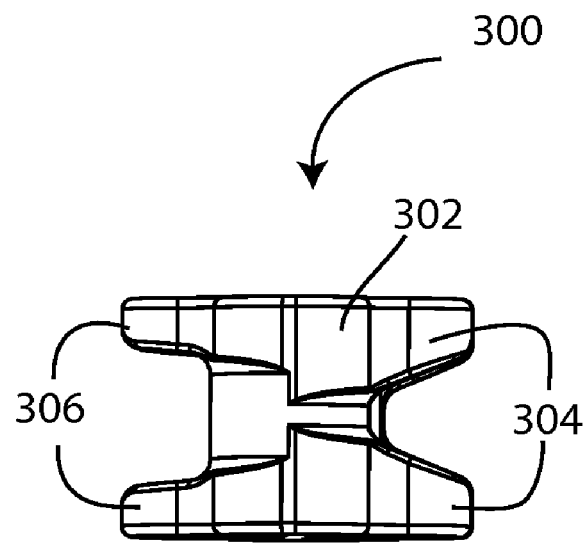
FIG. 16B is a posterior view of the implant of FIG. 16A.

FIGS. 16-18 illustrate alternative embodiments of implants with spacers which may expand in the anterior and/or posterior direction after implantation. FIGS. 16A is a lateral perspective view of an implant 300 which comprises a spacer 302, paired inferior flexible flanges 304 and paired superior flexible flanges 306. FIG. 16B is a posterior view of implant 300. The spacer 302 comprises a first spacer portion 308 and a second spacer portion 309, which are connected by the flexible flanges 304, 306. The spacer 302 is configured so that it may be pinched or squeezed down to a size which may be inserted from a lateral approach into the interspinous gap. Once inserted, the implant 300 may be rotated into a preferred orientation so that the paired inferior flexible flanges 304 engage and retain the lateral sides of the inferior spinous process, and the paired superior flexible flanges 306 engage and retain the lateral sides of the superior spinous process. The spacer may then be released and the first and second spacer portions 308, 309 allowed to expand along the anterior/posteriorly direction between the spinous processes. The configuration of the spacer portion 302 may provide a uniform extension stop at a minimum separation distance.

Figure 17A:
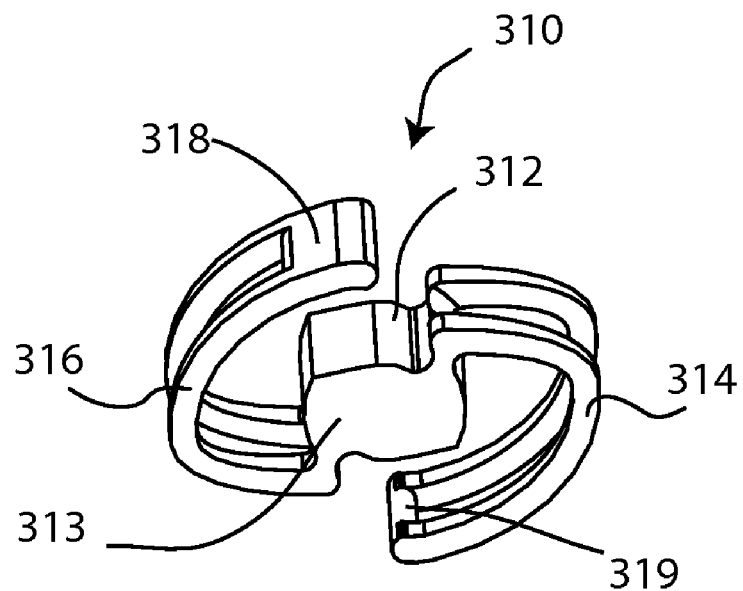
FIG. 17A is a lateral perspective view of an alternative embodiment of an interspinous spacer implant.
Figure 17B:
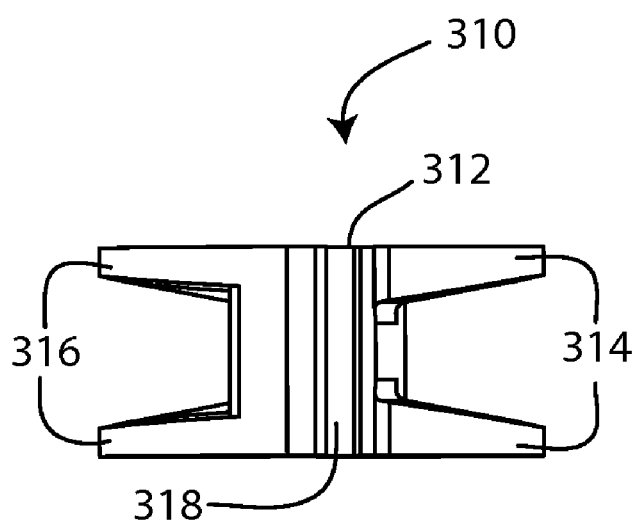
FIG. 17B is a posterior view of the implant of FIG. 17A.

Referring to FIGS. 17A and 17B, lateral and posterior views of implant 310 are shown. Implant 310 comprises a spacer 312, paired inferior flexible flanges 314 and paired flexible superior flanges 316. Spacer 312 further comprises a central portion 313, a superior portion 318 connected to the central portion by the flexible superior flanges 316, and an inferior portion 319 connected to the central portion by the flexible inferior flanges 314.

Figure 18A:
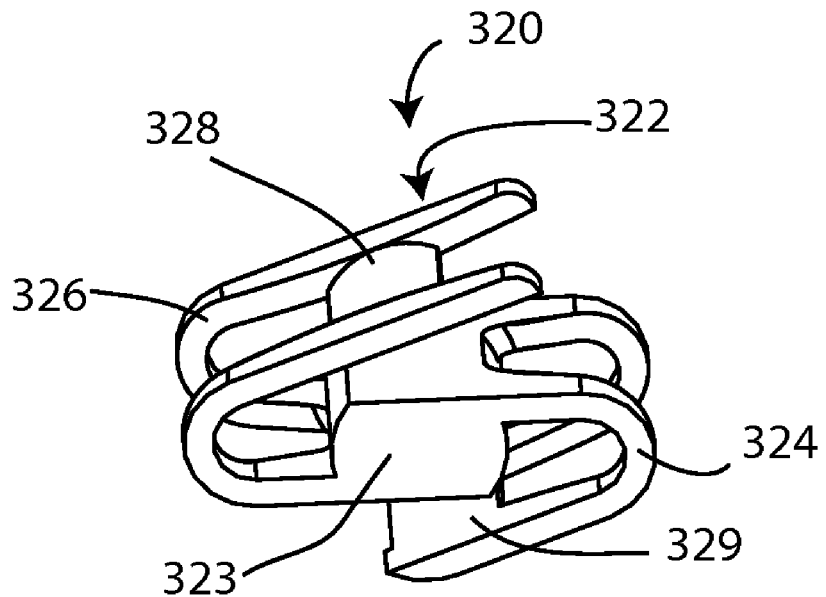
FIG. 18A is a lateral perspective view of an alternative embodiment of an interspinous spacer implant.
Figure 18B:
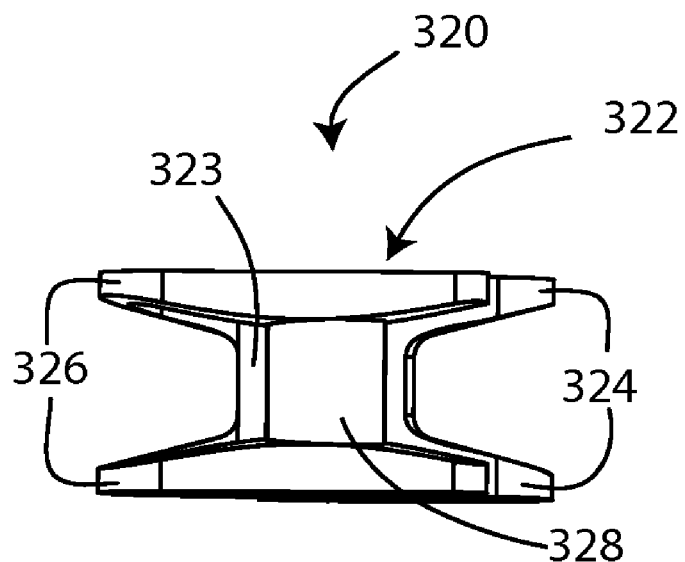
FIG. 18B is a posterior view of the implant of FIG. 18A.

Referring to FIGS. 18A and 18B, lateral and posterior views of implant 320 are shown. Similar in configuration to implant 310, implant 320 comprises a spacer 322, paired inferior flanges 324 and paired superior flanges 326. Spacer 322 further comprises a central portion 323, a superior portion 328 connected to the central portion by the flexible superior flanges 326, and an inferior portion 329 connected to the central portion by the flexible inferior flanges 324. The paired superior flanges 326 extend caudally past the spacer 322, such that when implanted and rotated, the extended ends of the paired superior flanges 326 may be adjacent the lateral sides of the inferior spinous process.

Implants 310 and 320 may be implanted in a similar manner to one another. The superior and inferior portions of the spacer may be pinched or squeezed toward the central portion of the spacer, creating a shape sized to fit into the interspinous gap, with the superior flexible flanges oriented anteriormost and the inferior flexible flanges oriented posteriormost. The implant is placed in the interspinous gap and rotated into a preferred orientation so that the paired inferior flexible flanges engage and retain the lateral sides of the inferior spinous process, and the paired superior flexible flanges engage and retain the lateral sides of the superior spinous process. The spacer may then be released and the superior and inferior portions of the spacers allowed to expand anteriorposteriorly between the spinous processes. Implants 300, 310 and 320 may provide a uniform extension stop at a minimum separation distance, and may also provide progressively increasing resilient force as the spinous processes converge during extension of the spine. Optionally, a tether such as that set forth previously may cooperate with the flanges to retain implant relative to a spinous process.

Figure 19A:
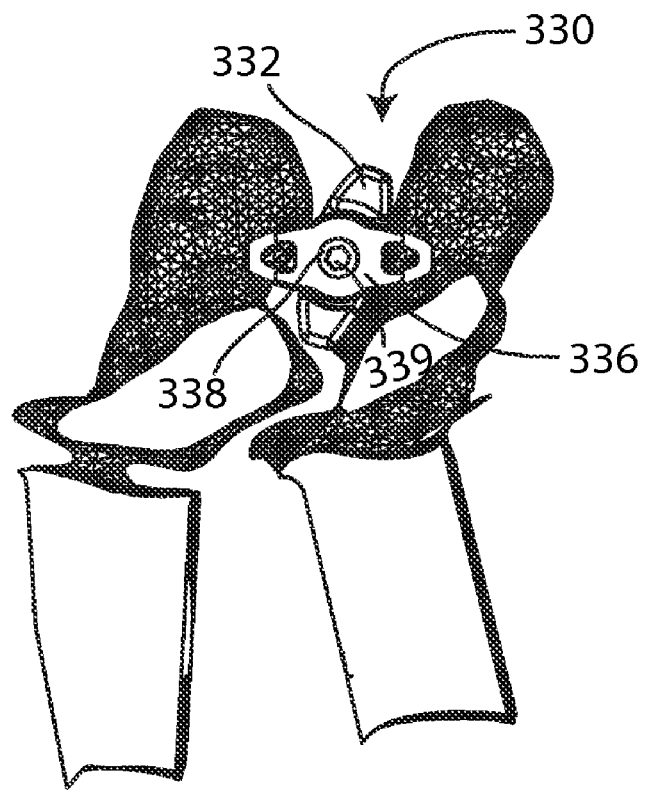
FIG. 19A is a lateral view of an alternative embodiment of an interspinous spacer implant, implanted between two vertebrae in a portion of a spine.
Figure 19B:
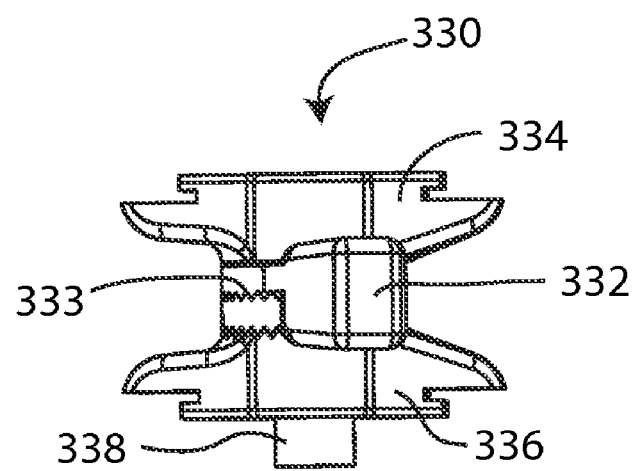
FIG. 19B is a posterior view of the implant of FIG. 19A.

Referring to FIGS. 19A and 19B, lateral and posterior views of an alternate interspinous spacer implant 330 is shown. Implant 330 comprises a spacer 332 which may be elongated in an anterior-posterior dimension, lateral flanges 334 and 336, and adjustment member 338, which may be a threaded bolt. Implant 330 is configured so that the lateral flanges 334, 336 may be rotated into and out of alignment with the spacer 332. Spacer 332 may comprise more than one component part, and may include teeth 333 which mesh when the adjustment member 338 is actuated. When the flanges are aligned in profile with the spacer, the implant has a size and shape which allows it to be inserted into the interspinous gap from a unilateral approach. Once in the interspinous gap, the flanges 334, 335 may be rotated relative to the spacer 332 so the flange ends are lateral to and engage the superior and inferior spinous processes 36, 56, as seen in FIG. 19A. The adjustment member 338 may be actuated or tightened to lock down the alignment of the flanges 334, 336 relative to the spacer 332. The adjustment member 338 may also have an insertion feature 339, which may function as an attachment point for tools used in inserting and adjusting the implant. Implant 330 may provide a uniform extension stop at a minimum separation distance.

Figure 20A:
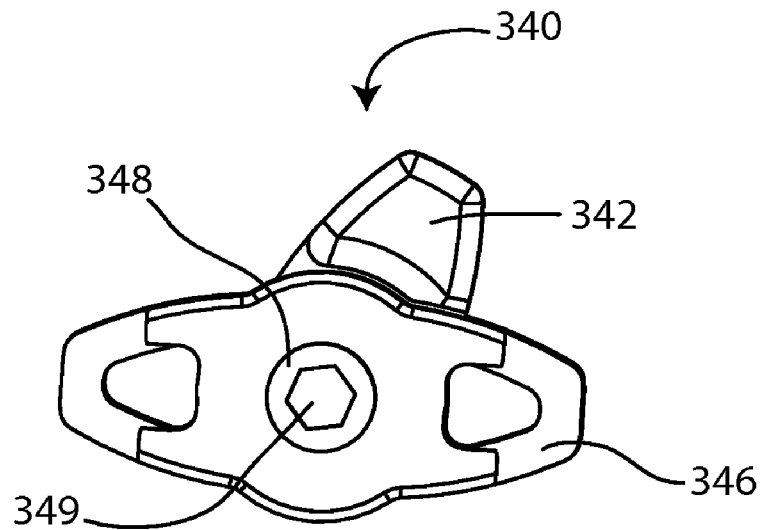
FIG. 20A is a lateral view of an alternative embodiment of an interspinous spacer implant.
Figure 20B:
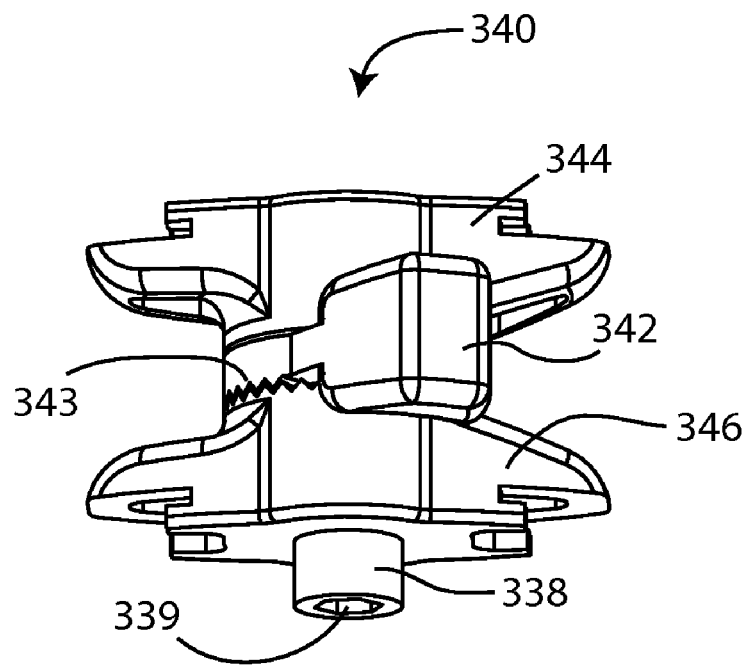
FIG. 20B is a posterior view of the implant of FIG. 20A.

Referring to FIGS. 20A and 20B, lateral and posterior views of an alternate interspinous spacer implant 340 is shown. Implant 340 is similar in configuration to implant 330, with the difference that a spacer 342 is elongated only in a posterior orientation. Implant 340 comprises the spacer 342, lateral flanges 344, 346 and an adjustment member 338. Spacer 342 may include teeth 343, which may mesh with teeth on either or both flanges 344, 346. The adjustment member 338, which may be a threaded bolt, may include an insertion feature 339 which may mate with insertion and/or adjustment tools (not shown). Implant 340 may be inserted and the flanges 344, 346 rotated in the same manner as previously set forth for implant 330. Implant 340 may provide a uniform extension stop at a minimum separation distance.

Figure 21A:
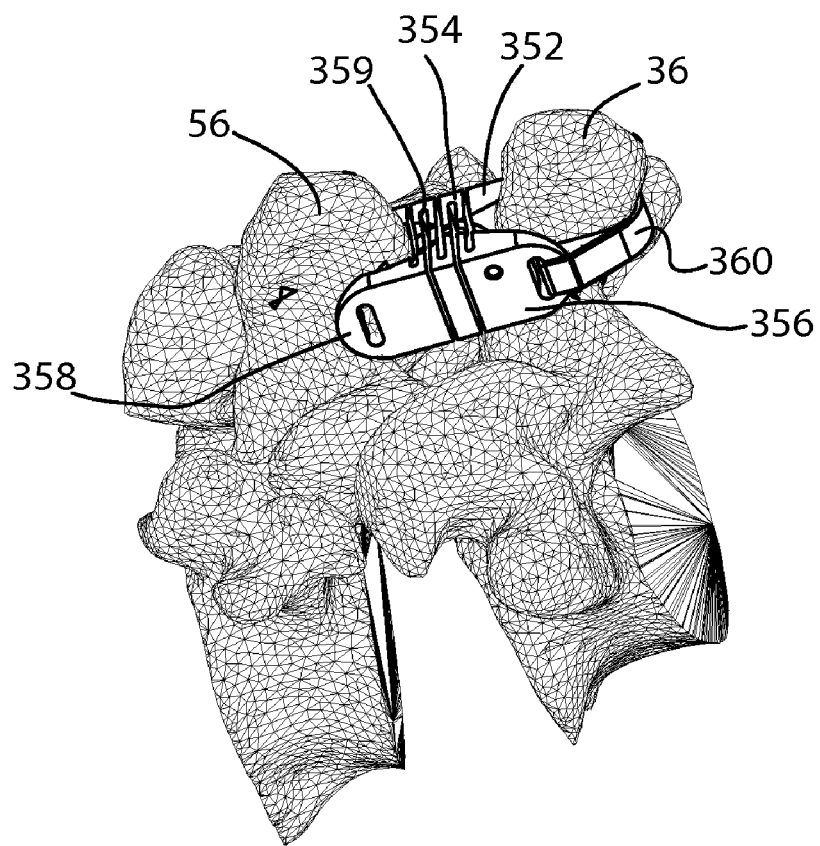
FIG. 21A is a posterior-lateral view of an alternative embodiment of an interspinous spacer implant with a tether, implanted between two vertebrae in a portion of a spine.
Figure 21B:
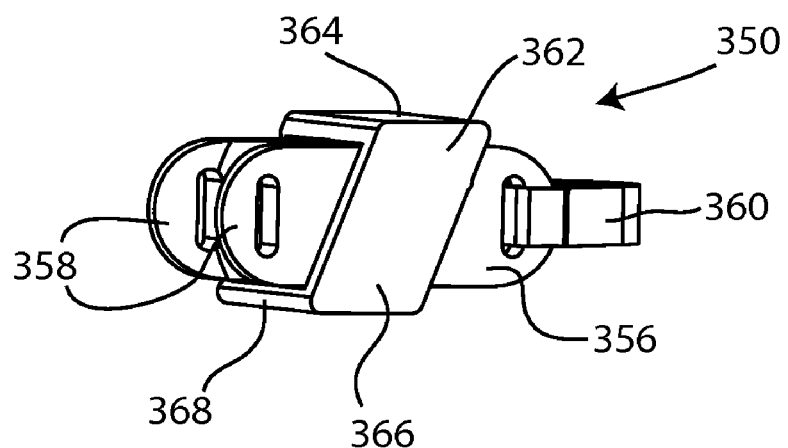
FIG. 21B is a cepahalad-lateral view of the implant of FIG. 21A.

FIGS. 21A and 21B illustrate an implant system 350 which may optionally be enhanced in the anterior-posterior dimension. Referring to FIG. 21A, implant 352 is generally H-shaped, with a centrally located spacer 354, a pair of inferior flanges 356 and a pair of superior flanges 358. The spacer 354 has a plurality of cutouts 359 which may be linear in orientation, to add flexibility to the spacer. A tether 360 loops around spinous process 36 and is attached to the inferior flanges 356. Optionally, but not shown, a second tether may be attached to the superior flanges 358 and loop around the superior spinous process 56. Referring to FIG. 21B, an optional blocker element 362 may be slid laterally onto the implant 352 after the implant is implanted between the spinous processes. The blocker element has three sides: a posterior side 364, a lateral side 366 and an anterior side 368, and is sized and shaped to overlap the implant 352 in the area of the spacer 354. The blocker element may increase the anterior-posterior dimension of the system 350. Additionally, the blocker element may modify the intrinsic compliance of the system. Whereas the flexible spacer 354 may provide a compliant extension stop between the spinous processes, the blocker element 362 may provide a rigid extension stop. The anterior 368 and/or posterior 364 sides of the blocker element 362 may be narrower than the spacer 354, in which case both compliant and rigid stops may be provided by the system 350.

Figure 22A:
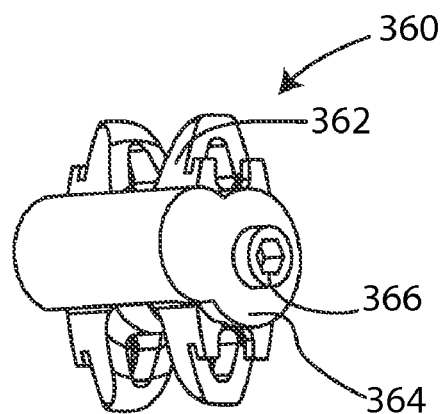
FIG. 22A is a posterior-lateral view of an alternative embodiment of an interspinous spacer implant.
Figure 22B:
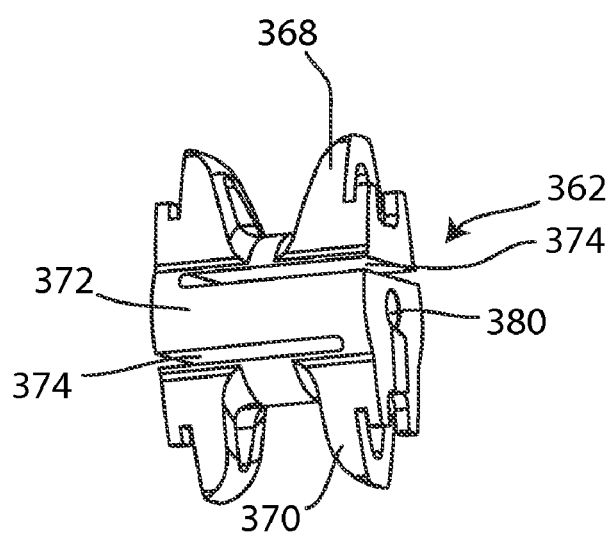
FIG. 22B is a posterior-lateral view of a spacer of the implant of FIG. 22A.
Figure 22C:
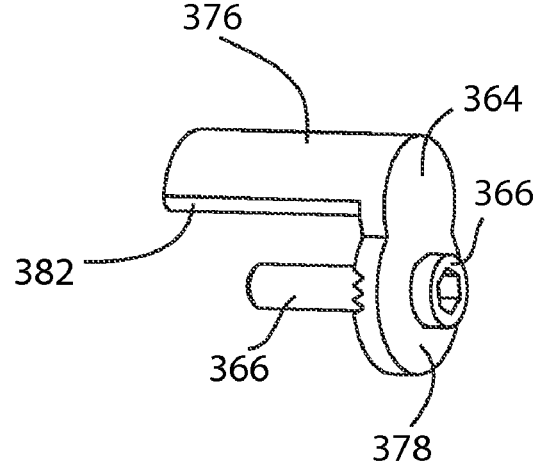
FIG. 22C is a cephalad-lateral view of a blocker element of the implant of FIG. 22A.

Referring to FIG. 22A, a posterior perspective view of an alternate embodiment of a spinous process spacer is shown. Implant 360 includes a spacing element 362 which includes a fixation portion, a blocker element 364, and an assembly pin 366. As seen in FIG. 22B, the spacing element 362 comprises a spacer 372 coupled to inferior flanges 368 and superior flanges 370. Grooves 374 are incised into the spacer 372 on the inferior and superior sides. As seen in FIG. 22C, the blocker element 364 comprises a posterior block 376 and a lateral face 378. The assembly pin 366, which may be threaded, may pass through a hole in the lateral face 378, then into a bore 380 in the spacer 372 to fasten the blocker element 364 to the spacing element 362, as seen in FIG. 22A. Additionally, one or more tabs 382 on the block 376 may slide into the grooves 374 on the spacer 372, further securing the blocker element 362 to the spacing element 362.

Implant 360 may be assembled in situ in the interspinous gap. Spacing element 362 may be inserted between the spinous processes and rotated until the inferior flanges 368 flank the inferior spinous process, and the superior flanges 370 flank the superior spinous process. Next the assembly pin 366 may be passed through the hole in the lateral face 378 of the blocker element 364. Together the blocker element 364 and assembly pin 366 are assembled, from a lateral approach, onto the spacing element 362 in situ, with the assembly pin 366 fitting into the bore 380, and tabs 382 sliding into the grooves 374. Once at a desired position, the blocker element 364 may be locked in place by tightening the assembly pin 366. The blocker element 364 may be comprised of a pliable material that provides a soft extension stop, while the spacer 372 provides a hard extension stop at a minimum separation distance. The blocker element 364 increases the anterior-posterior dimension of the implant.

Figure 23:
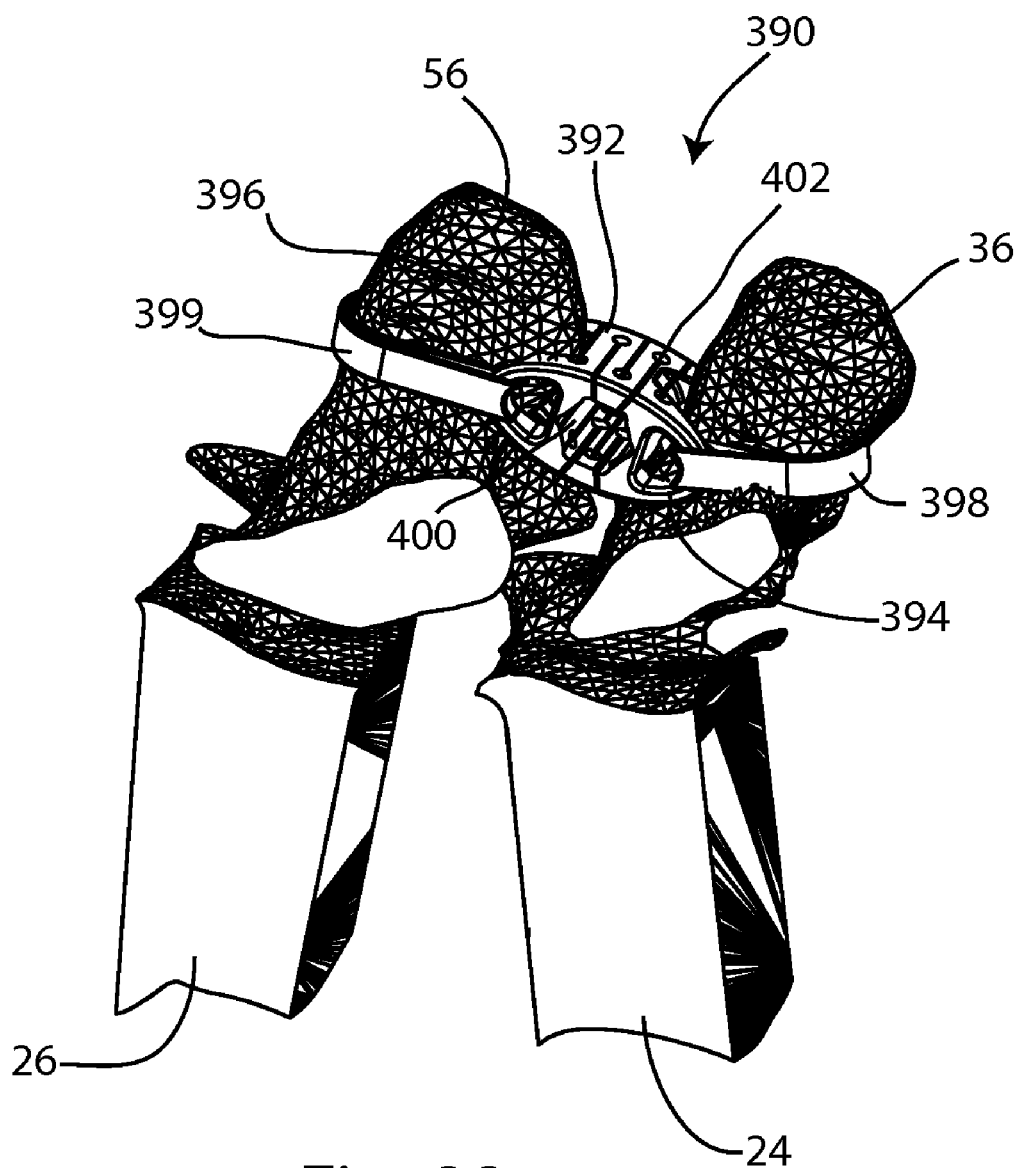
FIG. 23 is a lateral perspective view of an alternative embodiment of an interspinous spacer implant with two tethers, implanted between two vertebrae in a portion of a spine.

Referring to FIG. 23, an interspinous spacer implant with optional tethers is illustrated, implanted between two vertebrae 24, 26. Implant 390 comprises spacer 392, paired inferior flanges 394, and paired superior flanges 396. An inferior tether 398 is secured around the inferior spinous process 36, and a superior tether 399 is secured around the superior spinous process 56. The combination of flanges and tether(s) secures the spacer to one of the spinous processes, snugly or loosely as appropriate. Thus the spacer stays in its installed location in extension, due to the pinching action of the spinous processes against the central spacer portion and the action of the flanges against the sides of the spinous process. It also stays in place in flexion due to the action of the tether around one of the spinous processes.

The spacer 392 comprises a cavity 400 which extends the full lateral width of the spacer. The cavity 400 may have a specific shape, such as a hexagon, enabling it to also serve as an insertion feature which can connect with tools or instruments which provide torque to rotate the spacer. A plurality of slots 402 extend partially across the spacer 392, giving the spacer additional flexibility during extension and flexion. The implant 390 may be available in a variety of sizes, and in a variety of anterior-posterior dimensions.

Figure 24A:
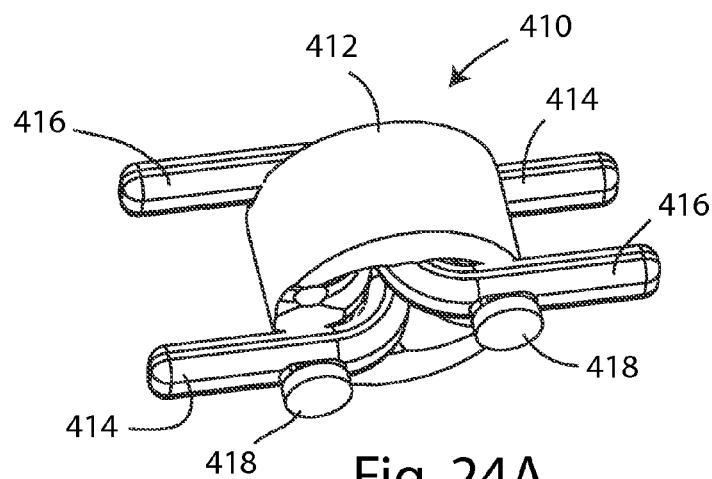
FIG. 24A is a posterior-lateral view of an alternative embodiment of an interspinous spacer implant.
Figure 24B:
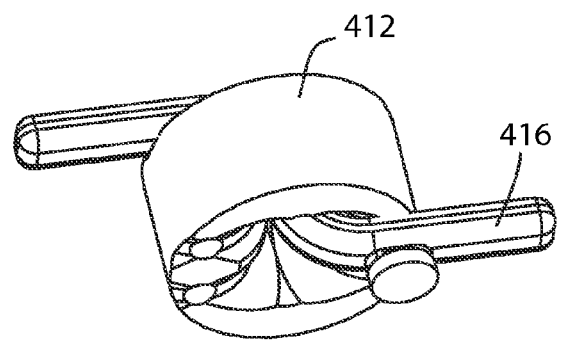
FIG. 24B is a posterior-lateral view of a spacer and a flange crossbar of the implant of FIG. 24A.
Figure 24C:
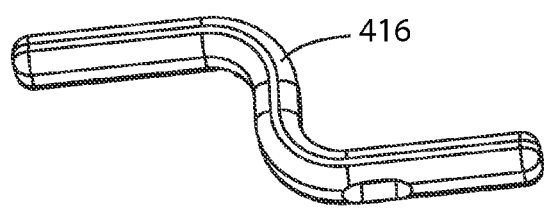
FIG. 24C is a posterior-lateral view of the flange crossbar of FIG. 24B.

FIG. 24A illustrates another alternative embodiment of an interspinous spacer. Implant 410 comprises a cylindrical spacer 412, a fixation portion which comprises two flange crossbars 414, 416, and may include one or more fasteners 418. As seen in FIG. 24C, each crossbar 414, 416 has a general Z shape such that one end of the crossbar may be positioned to a location adjacent an inferior spinous process, while the opposite end may simultaneously be located adjacent the opposite lateral side of a superior spinous process. Implant 410 may be assembled in situ. Spacer 412 may be placed into the interspinous gap from a lateral approach. One flange crossbar such as crossbar 416 is inserted through the spacer, as seen in FIG. 24B. The second flange crossbar 214 is then inserted through the spacer; however the crossbars 214, 216 may be inserted in either order. Once both crossbars 414, 416 are in place so that their ends flank and engage the superior and inferior spinous processes, fasteners 418 may be inserted through openings in the crossbars and the spacer to couple the crossbars to the spacer and lock the positions of the crossbars. Alternately, the crossbars may have integral elements which allow for a snap fit to the spacer 412. Implant 410 may allow a variable extension stop in which the spacer 412, or a portion thereof, is compliant and provides a soft extension stop, while the crossbars that pass through the center of the spacer provide a hard extension stop.

Figure 25:
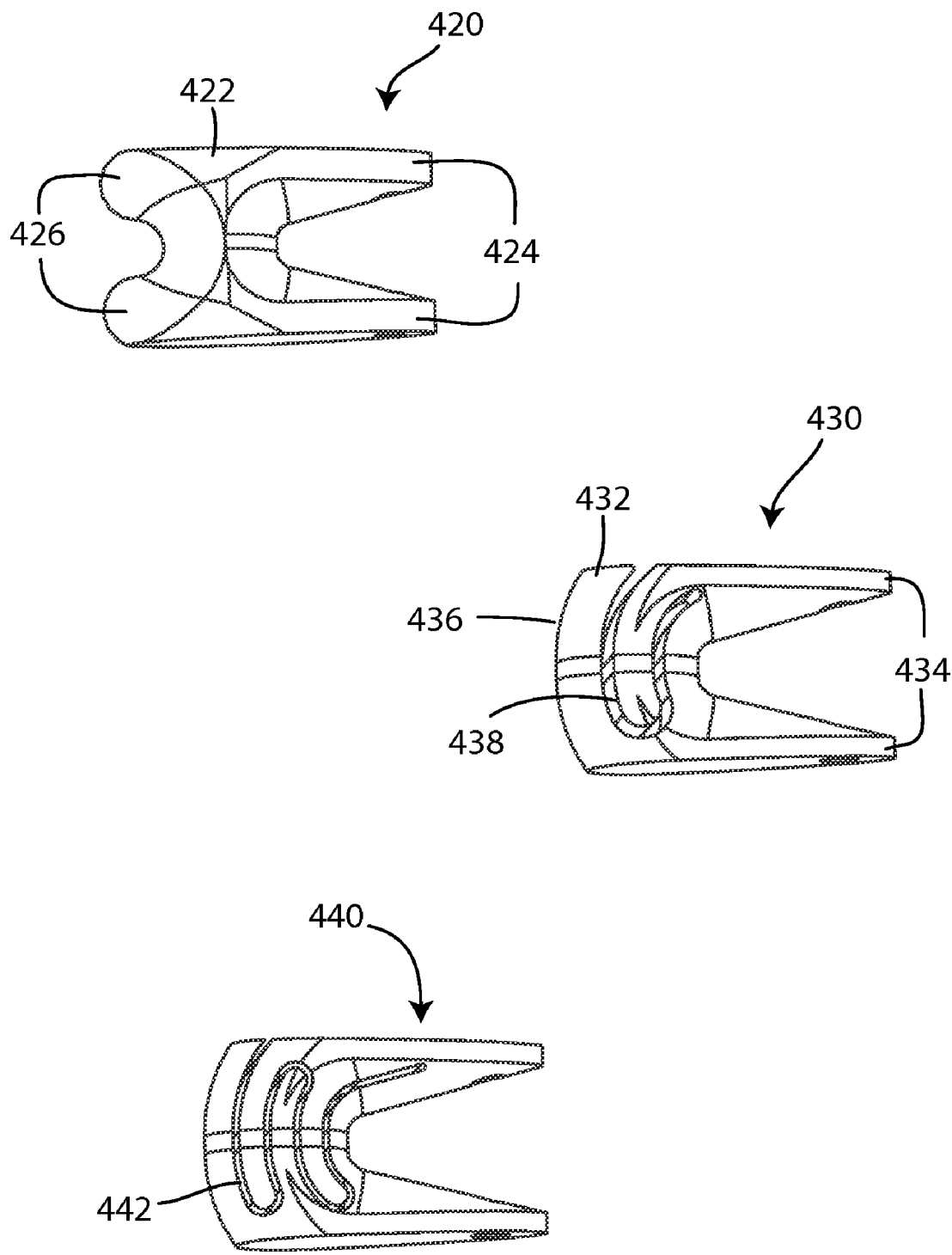
FIG. 25 is a posterior perspective view of three alternative embodiments of an interspinous spacer implant.

Referring to FIG. 25, three alternative interspinous spacer implants are shown. Implant 420 comprises a spacer 422, a pair of elongated inferior flanges 424, and a pair of truncated, rounded superior extensions 426. Implant 420 may comprise a flexible material, and is shaped to be implanted between the spinous processes from a lateral approach. A tether such as those described previously may be optionally secured to the inferior flanges 424 and looped around the inferior spinous process.

Implant 430 comprises a spacer 432 and fixation portion which is a pair of inferior flanges 434. The spacer 432 has a rounded superior wall 436, creating an arcuate shape which provides a uniform extension stop regardless of the relative orientation of the spinous processes through a range of motion. A slot 438 is cut in a curved pattern through the spacer 432, providing additional flexibility to the spacer. Implant 440 is similar in configuration to implant 430, except that a slot 442 is longer and arranged in more curves through the spacer, and may extend into one or both flanges. Both implants may provide a nonlinear increase in resilient force during extension, as the portions of the spacer cut by the slot sequentially deflect as the spacer is deformed by compression between the spinous processes. A tether may be coupled to either implant to retain the implant to a spinous process.

Figure 26:
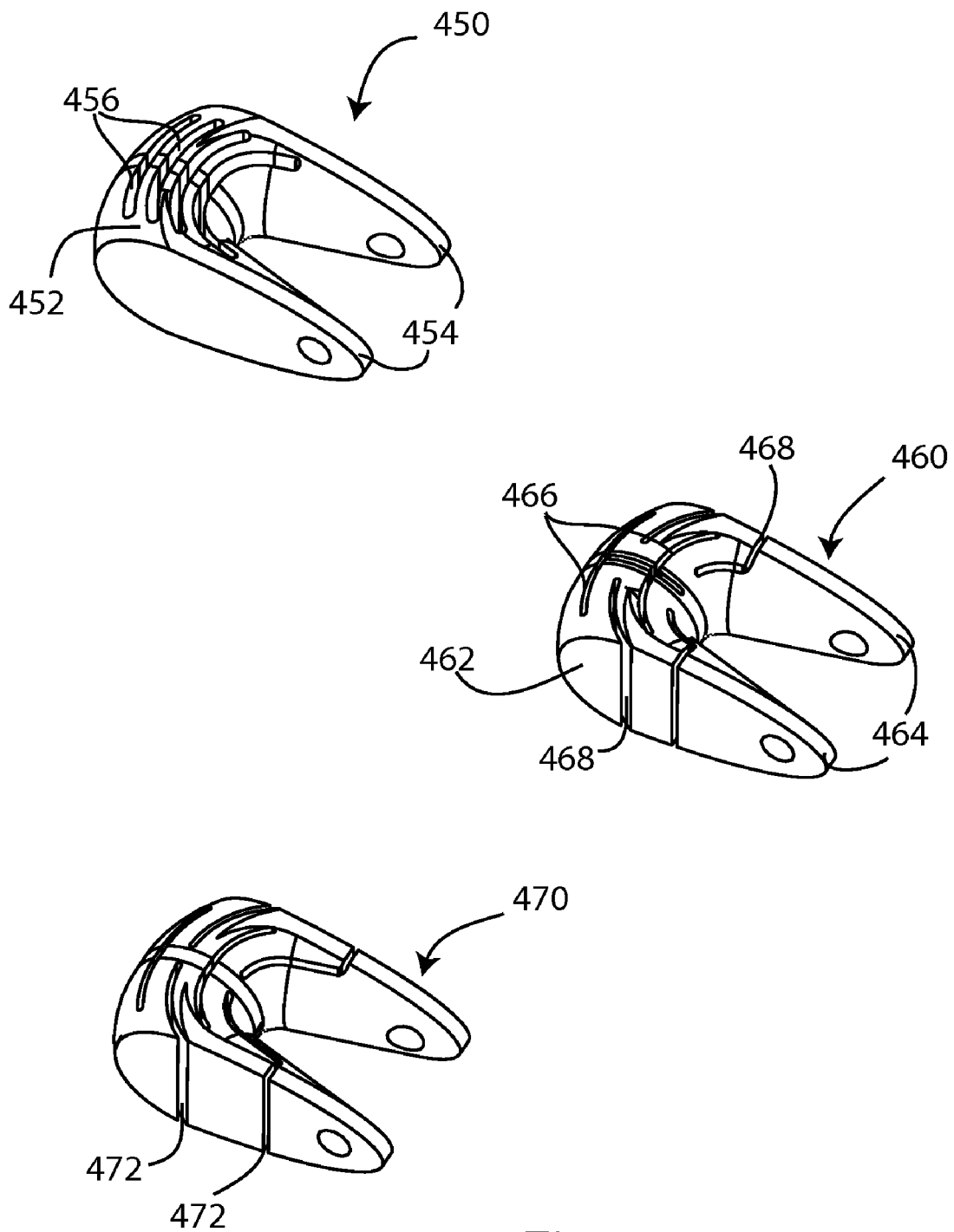
FIG. 26 is a posterior-lateral view of three alternative embodiments of an interspinous spacer implant.

FIG. 26 illustrates three additional alternative interspinous spacer implants. Implant 450 comprises a spacer 452 and a pair of flanges 454. The spacer 452 has a plurality of cutouts 456 which are openings through the spacer that do not open out to the lateral sides. Implant 420 may provide a nonlinear increase in resilient force during extension, as the portions of the spacer cut by the cutouts sequentially deflect as the spacer is deformed by compression between the spinous processes.

Implant 460 comprises a spacer 462 and a pair of flanges 464. Several cutouts 466 are incised through the spacer 462, and a plurality of slots 468 extend medially from the lateral sides of the spacer and the flanges. Implant 470 is similar in configuration to implant 470, except that slots 472 are longer, extending medially farther toward the center of the implant, and are located farther along the length of the flanges. It is appreciated that a variety of alternative implants could include cutouts and slots of various lengths, widths, depths and locations. The cutouts and slots may be sized and placed to create preferred levels of compliance and resilient force in the implants.

Implants 420, 430, 440, 450, 460, and 470 are sized and shaped to be implanted using a lateral approach from either side of the spinal column, and without disturbing the supraspinous ligament. Each implant may be held in an anterior-posterior orientation, with the flanges posteriormost, and inserted into the interspinous gap in that orientation. After the implant is at a desired lateral position, the spacer may be rotated so that the inferior flanges flank and engage the lateral sides of the inferior spinous process. The spacer stays in its installed location in extension, due to the pinching action of the spinous processes against the central spacer portion and the action of the flanges against the sides of the spinous process. Optionally, a tether may be coupled to any of the implants to retain the implant to the inferior spinous process.

Figure 27:
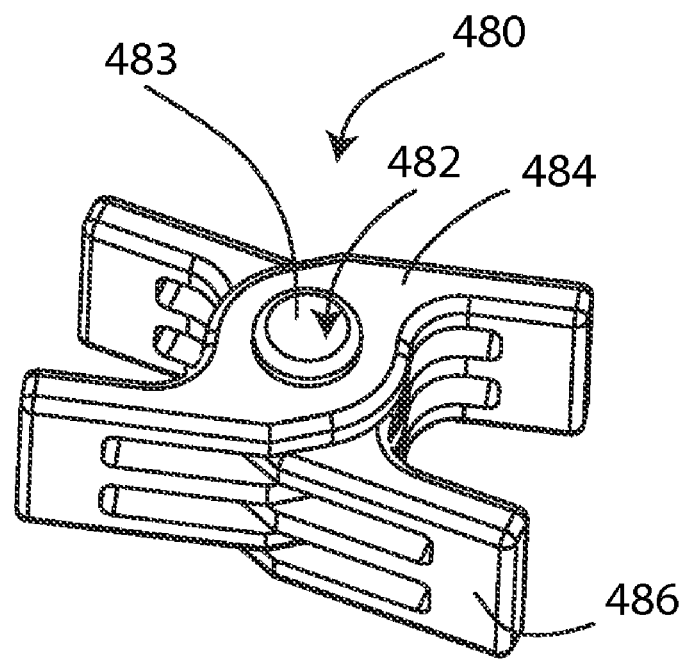
FIG. 27 is a posterior-lateral view of two alternative embodiments of an interspinous spacer implant.
Figure 27:
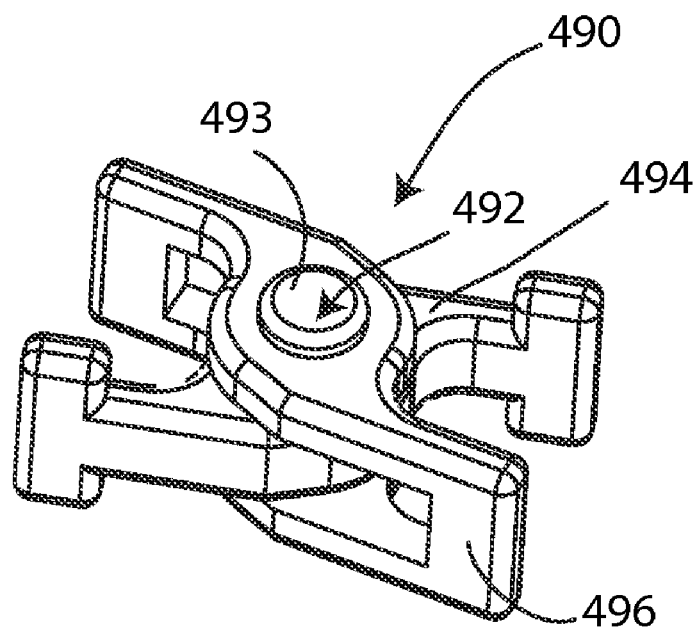

Referring to FIG. 27, two alternative embodiments of an interspinous spacer are shown. Implant 480 is generally X-shaped, and has flanges which are adjustable by way of a scissor-type hinge. A central pin 482 is generally cylindrical, may be threaded and has an adjustable end cap 483. The implant 480 also comprises a first diagonal flange 484 and a second diagonal flange component 486. The flange components 484, 486 are generally Z-shaped, and may be identical and differ only in their orientation in the assembled implant. Each flange component 484, 486 has a bore through which the central pin 482 fits. The spacing between the flange components 484, 486 may be adjusted by rotating the components 484, 486 about the central pin 482; then the end cap 483 may be fastened to lock down the implant at a preferred flange spacing. Alternately, the central pin and end cap may comprise a spring or ratchet which provides pressure to the flanges, allowing the flanges to grip the spinous processes.

Similar to implant 480, implant 490 has a central pin 492 and may have an end cap 493. The implant also comprises an inner diagonal flange component 494 and an outer diagonal flange component 496. The flange components 494, 496 hinge around the central pin 492. The orientation of the flange components 494, 496 may be adjusted by rotating around the central pin 492. Like implant 480, the central pin may comprise a spring, ratchet or other member to provide pressure to the flanges.

Implants 480, 490 may be implanted using similar methods. An approach to either lateral side of the spine may be used. The implant 480 or 490 is "flattened" by loosening the end cap and compressing the flange components toward one another until the implant has a flat profile, with little space between the flanges, and the end cap may be tightened to hold this profile. The implant is inserted into the interspinous gap. The flanges are released and allowed to close around the spinous processes.

The implants, or components thereof, disclosed herein may be monolithic, or unitary, formed as one piece. The implants disclosed herein may also be non-fillable, which means that they are not configured to be inflated or filled with a separate substance such as a gas, liquid or solid in order to provide a desired dimension of spacing between adjacent spinous processes, or in order to secure a fixation portion to a spinous process. Non-fillable implants may comprise continuous construction with no chambers, balloons or other enclosable areas capable of containing a separate substance. The spacer members and other implant components disclosed herein may also be flexible, which means they may flex when subjected to sufficient force.

It is appreciated that implants disclosed herein may have spacers shaped to provide a consistent offset between the spinous processes, or the spacers may have a variable shape to provide a variable offset. For example, biomechanical studies could show that it is preferable to have a thicker offset either medially or laterally, in order to produce the desired effects throughout a range of motion. The implants may also provide initial progressive resistance to extension, followed by a definite extension stop. This may be achieved by intrinsic spring elements, compliant materials layered over rigid elements, or viscoelastic materials, among others. The actual proportions of compliant deflection combined with extension stop dimension are dictated primarily by patient anatomy and it is appreciated that a range of sizes would be required up to and possibly beyond a 25 mm (1") extension stop. The compliant deflection might be a percentage of the extension stop dimension, or a fixed increment.

All implants described herein may be implanted from a unilateral approach, that is, the implantation procedure may be completed from one lateral side of the spine, or the other side. The choice of sides may depend on surgeon preference or specific patient anatomic considerations. Implants which comprise the bracket 110 may be configured to be inserted, and attached to the spinous process from either lateral side. Additionally, implantation of the implants may occur without disturbing the supraspinous ligament.

The present invention may be embodied in other specific forms without departing from its spirit or essential characteristics. It is appreciated that various features of the above-described examples can be mixed and matched to form a variety of other alternatives. For example, the number of flanges can vary, as can the configuration of the spacer member. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implant comprising:
   a spacer sized to fit between first and second adjacent spinous processes of a human spine to urge the maintenance of a minimum separation between the first and second spinous processes; and
   a bracket coupled to the spacer, the bracket having
   an open configuration, in which the bracket is able to receive the first spinous process, and
   a closed configuration, in which the bracket is able to encircle at least a superior aspect, a lateral aspect, and an inferior aspect of the first spinous process to securely grip the first spinous process thereby holding the spacer in a stable position relative to the first spinous process;
   wherein the bracket toggles from the open configuration to the closed configuration to encircle at least the superior, lateral, and inferior aspects of the first spinous process when the open bracket is pushed against the lateral aspect of the first spinous process.

2. The implant of claim 1, wherein the bracket is shaped to toggle between the open and closed configurations in response solely to pressure urging the bracket toward the closed configuration.

3. The implant of claim 1, wherein the spacer and the bracket are formed as a single piece with each other.

4. The implant of claim 1, wherein the spacer is shaped to be inserted between the first and second spinous processes from a lateral approach, wherein the bracket is further shaped, in the open configuration, to receive the first spinous process when inserted along the lateral approach.

5. The implant of claim 1, wherein the second spinous process is superior to the first spinous process such that, after toggling of the bracket to the closed configuration to at least partially encircle the first spinous process, the spacer is shaped to be positioned superior to the bracket.

6. The implant of claim 1, wherein the bracket has a C-shaped configuration comprising a first end and a second end defining a gap between them, wherein in response to toggling of the bracket to the closed configuration, the gap shrinks to restrict withdrawal of the first spinous process from within the bracket.

7. The implant of claim 6, wherein the bracket further comprises a spring member that is transformable between a first low energy shape and a second low energy shape, wherein transforming the spring member from the first low energy shape to the second low energy shape toggles the bracket from the open position to the closed position.

8. The implant of claim 1, wherein the spacer comprises a generally arcuate shape within a coronal plane of the spine, wherein the generally arcuate shape is oriented toward the second spinous process to help provide a uniform extension stop between the first spinous process and the second spinous process.

9. The implant of claim 1, wherein the spacer has a resilient configuration selected to provide variable resistive force urging the first and second spinous processes apart in response to extension of the spine.

10. The implant of claim 9, wherein the spacer is further configured to provide an extension stop that substantially prevents motion of the second spinous process toward the first spinous process beyond a threshold extension level.

11. An implant comprising:
    a spacer sized to fit between first and second adjacent spinous processes of a human spine to urge the maintenance of a minimum separation between the first and second spinous processes; and
    a fixation portion coupled to the spacer, wherein the fixation portion is configured to be coupled to the first spinous process to retain the spacer relative to the first spinous process;
    wherein the spacer comprises a generally arcuate shape within a coronal plane of the spine, wherein, when the spacer is between the first and second spinous processes, a convex wall of the generally arcuate shape is oriented toward the second spinous process and the convex wall extends bilaterally beyond the first and second spinous processes;
    wherein the second spinous process is superior to the first spinous process such that, after coupling the fixation portion to the first spinous process, the spacer is shaped to be positioned superior to the fixation portion.

12. The implant of claim 11, wherein the spacer and the fixation portion are formed as a single piece with each other.

13. The implant of claim 11, wherein the spacer is shaped to be inserted between the first and second spinous processes from a lateral approach, wherein the fixation portion is shaped to be coupled to the first spinous process when inserted along the lateral approach.

14. The implant of claim 11, wherein the fixation portion comprises a bracket having an open configuration, in which the bracket is able to receive the first spinous process, and a closed configuration, in which the bracket at least partially encircles the first spinous process to securely grip the first spinous process thereby holding the spacer in a stable position relative to the first spinous process.

15. The implant of claim 11, wherein the spacer has a resilient configuration selected to provide variable resistive force urging the first and second spinous processes apart in response to extension of the spine.

16. The implant of claim 15, wherein the spacer is further configured to provide an extension stop that substantially prevents motion of the second spinous process toward the first spinous process beyond a threshold extension level.

17. The implant of claim 11, further comprising:
    a tether configured to cooperate with the remainder of the implant to fully encircle a selected one of the first or second spinous processes to retain the implant relative to the selected spinous process.

18. An implant comprising:
- a spacer sized to fit between first and second adjacent spinous processes of a human spine to urge the maintenance of a minimum separation between the first and second spinous processes; and
- a fixation portion coupled to the spacer, wherein the fixation portion is configured to be coupled to the first spinous process to retain the spacer relative to the first spinous process;
- wherein the spacer comprises a plurality of resilient elements positioned to be sequentially deflected in response to deformation of the spacer to provide a non-linear increase in resilient force with deflection of the spacer;
- wherein, when the spacer is between the first and second spinous processes and the fixation portion is coupled to the first spinous process, the implant only engages a single side of the second spinous process, wherein the side is selected from the group consisting of the superior side and the inferior side.

19. The implant of claim 18, wherein the spacer and the fixation portion are formed as a single piece with each other.

20. The implant of claim 18, wherein the spacer is shaped to be inserted between the first and second spinous processes from a lateral approach, wherein the fixation portion is further configured to be coupled to the first spinous process when inserted along the lateral approach.

21. The implant of claim 18, wherein the fixation portion comprises a bracket having an open configuration, in which the bracket is able to receive the first spinous process, and a closed configuration, in which the bracket at least partially encircles the first spinous process to securely grip the first spinous process thereby holding the spacer in a stable position relative to the first spinous process.

22. The implant of claim 18, wherein the second spinous process is superior to the first spinous process such that, after coupling the fixation portion to the first spinous process, the spacer is shaped to be positioned superior to the fixation portion.

23. The implant of claim 18, wherein each resilient element is coupled to the fixation portion such that after the fixation portion is coupled to the first spinous process each resilient element extends substantially perpendicular to the first spinous process.

24. The implant of claim 18, wherein the resilient elements are concentrically arranged relative to each another.

25. The implant of claim 18, further comprising:
- a tether configured to cooperate with the remainder of the implant to fully encircle a selected one of the first or second spinous processes to retain the implant relative to the selected spinous process.

26. An implant comprising:
- a spacer sized to fit between first and second adjacent spinous processes of a human spine to urge the maintenance of a minimum separation between the first and second spinous processes; and
- a fixation portion coupled to the spacer, wherein the fixation portion is configured to be coupled to the first spinous process to retain the spacer relative to the first spinous process;
- wherein the spacer comprises a generally arcuate shape within a coronal plane of the spine, wherein, when the spacer is between the first and second spinous processes, a convex wall of the generally arcuate shape is oriented toward the second spinous process and the convex wall extends bilaterally beyond the first and second spinous processes;
- wherein the spacer has a resilient configuration selected to provide variable resistive force urging the first and second spinous processes apart in response to extension of the spine;
- wherein the spacer is further configured to provide an extension stop that substantially prevents motion of the second spinous process toward the first spinous process beyond a threshold extension level.

27. The implant of claim 26, wherein the spacer and the fixation portion are formed as a single piece with each other.

28. The implant of claim 26, wherein the spacer is shaped to be inserted between the first and second spinous processes from a lateral approach, wherein the fixation portion is shaped to be coupled to the first spinous process when inserted along the lateral approach.

29. The implant of claim 26, wherein the fixation portion comprises a bracket having an open configuration, in which the bracket is able to receive the first spinous process, and a closed configuration, in which the bracket at least partially encircles the first spinous process to securely grip the first spinous process thereby holding the spacer in a stable position relative to the first spinous process.

30. The implant of claim 26, wherein the second spinous process is superior to the first spinous process such that, after coupling the fixation portion to the first spinous process, the spacer is shaped to be positioned superior to the fixation portion.

31. The implant of claim 26, further comprising:
- a tether configured to cooperate with the remainder of the implant to fully encircle a selected one of the first or second spinous processes to retain the implant relative to the selected spinous process.

* * * * *